US011447446B2

(12) United States Patent
Zhou et al.

(10) Patent No.: US 11,447,446 B2
(45) Date of Patent: Sep. 20, 2022

(54) PROCESS OF FLUORINATING INORGANIC OR ORGANIC COMPOUNDS BY DIRECT FLUORINATION

(71) Applicant: Fujian Yongjing Technology Co., Ltd, Shaowu (CN)

(72) Inventors: Changyue Zhou, Shaowu (CN); Hongjun Du, Shaowu (CN); Wenting Wu, Shaowu (CN)

(*) Notice: Subject to any disclaimer, the term of this patent is extended or adjusted under 35 U.S.C. 154(b) by 31 days.

(21) Appl. No.: 16/907,188

(22) Filed: Jun. 20, 2020

(65) Prior Publication Data

US 2021/0053911 A1   Feb. 25, 2021

(30) Foreign Application Priority Data

Aug. 22, 2019  (DE) .......................... 102019122645.7

(51) Int. Cl.

| | | |
|---|---|---|
| *C07C 253/30* | (2006.01) | |
| *C01B 21/083* | (2006.01) | |
| *C07C 67/307* | (2006.01) | |
| *C07C 201/12* | (2006.01) | |
| *C07C 303/22* | (2006.01) | |
| *C07D 317/42* | (2006.01) | |
| *C07B 39/00* | (2006.01) | |

(52) U.S. Cl.
CPC ........ *C07C 253/30* (2013.01); *C01B 21/0835* (2013.01); *C07B 39/00* (2013.01); *C07C 67/307* (2013.01); *C07C 201/12* (2013.01); *C07C 303/22* (2013.01); *C07D 317/42* (2013.01)

(58) Field of Classification Search
None
See application file for complete search history.

(56) References Cited

U.S. PATENT DOCUMENTS

| 7,268,238 B2 * | 9/2007 | Woo ..................... C07D 317/36 549/296 |
|---|---|---|
| 2012/0220788 A1 * | 8/2012 | Lambert .............. C07D 317/42 549/229 |

FOREIGN PATENT DOCUMENTS

| EP | 0267627 | 5/1988 | |
|---|---|---|---|
| WO | WO-2018113628 A1 * | 6/2018 | ........... C07D 317/42 |

OTHER PUBLICATIONS

Lang ("Multiphase minireactor system for direct fluorination of ethylene carbonate" Chemical Engineering Journal, 179, 2012, p. 330-337) (Year: 2012).*

* cited by examiner

*Primary Examiner* — Amy C Bonaparte

(57) ABSTRACT

The invention relates to a use of a fluorination gas, and the elemental fluorine ($F_2$) is present in a high concentration, for example, in a concentration of elemental fluorine ($F_2$), especially of equal to much higher than 15 or even 20% by volume, and to a process for the manufacture of a fluorinated compound by direct fluorination employing a fluorination gas, wherein the elemental fluorine ($F_2$) is present in a high concentration. The process of the invention is directed to the manufacture of a fluorinated compound, for the exception of fluorinated benzene, by direct fluorination. Especially the invention is of interest in the preparation of fluorinated organic compounds, final products and as well intermediates, for usage in agro-, pharma-, electronics-, catalyst, solvent and other functional chemical applications. The fluorination process of the invention may be performed batch-wise or in a continuous manner.

6 Claims, 3 Drawing Sheets

PROCESS OF FLUORINATING INORGANIC OR ORGANIC COMPOUNDS BY DIRECT FLUORINATION

BACKGROUND OF THE INVENTION

Field of the Disclosure

The invention relates to process for the manufacture or preparation of fluorinated inorganic or organic compounds, respectively, using a fluorination gas comprising elemental fluorine ($F_2$). The process of the invention, for example, can comprise a batch or continuous manufacture or preparation of fluorinated inorganic or organic compounds, respectively, using fluorination gas comprising elemental fluorine ($F_2$).

Description of Related Art

Fluorinated organic compounds in industrial scale are prepared by fluorine halogen exchange using anhydrous HF, addition of HF to olefinic double bonds, fluorinating agents like amine×nHF, electrofluorination with HF (in situ generation of $F_2$) where in latter case selectivity, scalability and missing environmental friendliness (formation of very toxic partial fluorinated compounds) often is and remains an unsolved problem. Another existing fluorination procedure is using $F_2$-gas directly. But this requires—besides availability of industrial quantities—the very skilled handling of $F_2$-gas and co-produced HF (hydrogen (H) vs. fluorine (F) exchange reaction).

Elemental fluorine ($F_2$) is a yellow compressed gas (fluorine gas, $F_2$-gas) with a pungent odor; it is a strong oxidant, reacts violently with combustible and reducing substances. Due to its strong chemical activity, and therefore, the need of equipment and containers with strong corrosion resistance to fluorine and HF, $F_2$-gas is usually mixed with nitrogen ($N_2$). In Europe, usually only mixtures of 95% N2 with only 5% $F_2$-gas are allowed to be transported, or with exemption permission only of up to 10% content of $F_2$-gas.

In Asia, a ratio up to 20% $F_2$-gas in inert gas like $N_2$ is available.

Such dilution of $F_2$-gas by inert gas like $N_2$ is necessary because of safety and reducing and/or controlling the chemical activity or reactivity of $F_2$-gas in chemical reactions. However, this dilution of $F_2$-gas by inert gas needed for the said reason of "deactivation" in industrial scale has the disadvantage that on the one side the dosing of $F_2$-gas diluted by inert gas is very challenging, and on the other side even more important as drawback, that the heat transfer in reactor equipment during chemical reactions with $F_2$-gas, as these reaction are very exothermic, is very much reduced by inert gas, and due to the diluting inert gas is resulting in reduced heat transfer, and in worst case might even cause runaways. Hence, in principle the inert gas is undesirably functioning as insulation gas.

Meinert H., has reported about some reaction, and observed decomposition, of fluorine with pyridine at temperatures of −40° C. or −80° C. of fluorine diluted by nitrogen (ZeitschriftfürChemie, Leipzig, DeutscherVerlagfürGrundstoffindustrie, 1961-1990, ISSN 0044-2402, 1965, Volume 5 (2). Comments, Page 64, ZCM 1130 received on 7 Dec. 1964). Roger S. et al. have reported some reactions of $CF_3OF$ (trifluoromethylhypofluorite (Journal of the American Chemical Society Volume 79, 1957, 5625-5627). The document EP 0267627 A1 (Ausimont) describes a process for the preparation of halogenated polyethers, and e.g., is using $CF_3OF$ (trifluoromethylhypofluorite.

It is known in the prior art to fluorinate deactivated benzene derivatives with a diluted fluorination gas, e.g., in Chambers et al. (Journal of Fluorine Chemistry 128 (2007) 29-33). Chambers is using as a fluorination gas containing 10% (vol.-%) elemental fluorine ($F_2$) in nitrogen (N2) as inert gas, and is using solvents for the reaction, e.g., acetonitrile or formic acid reaction media. Chambers is reporting representative direct fluorination reactions of 1,4-disubstituted aromatic systems bearing an electron withdrawing and releasing group, using microreactor technology. The fluorinated products are obtained by a process consistent with an electrophilic substitution process due to the solvents used. Thus, high selectivity and yields of monofluorinated products are reported by Chambers when using either acetonitrile or formic acid reaction media. It is known in the prior art that high relative permittivity solvents or protonic acids can be used very effectively for the fluorination of aromatic systems because, in these media, the fluorine molecule is rendered more susceptible towards nucleophilic attack by interaction with the solvent while competing free radical processes are minimized. However, in the process described by Chambers, typically, reactions are carried out only in small scale reactions, for example over a 16 h period enabling 5 to 10 g of crude product to be collected.

Also, Chambers tested in the same experimental setting as described here above, the direct fluorination of aromatic rings bearing two strong electron withdrawing groups, which aromatic rings are, of course, relatively unreactive towards electrophilic attack. However, reactions between such substrates and elemental fluorine ($F_2$), i.e., using the fluorination gas containing 10% (vol.-%) elemental fluorine ($F_2$) in nitrogen (N2) as inert gas, and using a microreactor gave low conversions to fluorinated products, but in very selective, clean reactions. Nevertheless, also in this process described by Chambers, typically, reactions are carried out only in small scale reactions, for example over a 16 h period enabling 5 to 10 g of crude product to be collected.

Importantly, it must be noted that despite the successful conversions in the range of 78% to 91% of fluorination reactions on deactivated benzene derivatives with a diluted fluorination gas in acetonitrile as solvent, nevertheless Chambers did not test, and neither motivate for testing of non-deactivated benzene itself, nor any other (aromatic or non-aromatic) organic compound or any inorganic compound, neither in small-scale of 5 to 10 g product quantities nor in large-scale at all.

Accordingly, there is a high demand of enabling large-scale and/or industrial production of fluorinated inorganic compounds or organic compounds, respectively, by directly fluorinating an inorganic starting compound or organic starting compound, respectively, in a controlled and effective manner in a large-scale and/or industrial setting.

When producing fluorinated inorganic compounds or organic compounds, respectively, by directly fluorinating an inorganic starting compound or organic starting compound, respectively, in a controlled and effective manner, in another aspect it is also desired to minimize, or even to substantially avoid, the dilution of the elemental fluorine ($F_2$) by inert gas, e.g. by nitrogen (N2) as inert gas, and at least to enable the use of fluorination gas containing essentially higher concentrated elemental fluorine ($F_2$) than those concentrations described above and used in the prior art, e.g., essentially higher concentrated elemental fluorine ($F_2$) than 10% by volume as used by Chambers or available under exemption in Europe, or essentially higher concentrated elemental fluorine ($F_2$) than 20% by volume as available Asia.

It is an object of the present invention to provide a high efficient process for the manufacture or for preparation of fluorinated inorganic compounds or organic compounds, respectively, by direct fluorination using fluorine gas ($F_2$), wherein in the fluorination process a fluorine gas (fluorination gas) with concentrations of substantially more than, in particular very much higher than 15 or even 20% by volume of elemental fluorine ($F_2$), especially of equal to much higher than 25% by volume (i.e., at least 25% by volume) of elemental fluorine ($F_2$), preferably of equal to much higher than 35 or even 45% by volume of elemental fluorine ($F_2$), can be used for chemical synthesis, especially for the manufacture or for preparation of fluorinated inorganic compounds or fluorinated organic compounds, respectively, as final products and/or intermediates, for usage in agro-, pharma-, electronics-, catalyst, solvent and other functional chemical applications.

It is preferably an object of the present invention to provide a fluorination process for the manufacture or preparation of fluorinated inorganic compounds or fluorinated organic compounds, respectively, by direct fluorination using fluorine gas ($F_2$), by which it is possible to perform chemistry with a fluorination gas consisting essentially of $F_2$-gas as it directly comes out of the $F_2$-electrolysis reactors (fluorine cells), optionally only diluted for a minor degree, e.g., for adapting and controlling the fluorination process and its parameters.

It is preferably another object of the present invention to provide a fluorination process for the manufacture or preparation of fluorinated inorganic compounds or fluorinated organic compounds, respectively, by direct fluorination using fluorine gas ($F_2$-gas), by means of special equipment and special reactor design.

It is preferably still another object of the present invention to provide a fluorination process for the manufacture or preparation of fluorinated inorganic compounds or fluorinated organic compounds, respectively, by direct fluorination using fluorine gas ($F_2$-gas), wherein the process can be performed in a large-scale and/or industrial production of fluorinated inorganic compounds or organic compounds.

SUMMARY OF THE INVENTION

The objects of the invention are solved as defined in the claims, and described herein after in detail.

Regarding the scope of the present invention it is to be noted that, that for legal reason only but not for technical reason, there is a proviso that the organic starting compound, to be reacted with the fluorination gas, is not benzene, not benzoic acid, and not a benzoic acid derivative, and the fluorinated organic compound produced is not a fluorinated benzene, and in particular the fluorinated compound produced is not monofluorobenzene.

According to the objects, the present invention provides a high efficient process for the manufacture or for preparation of a fluorinated inorganic compound or fluorinated organic compound, respectively, by direct fluorination using fluorine gas ($F_2$), wherein in the fluorination process a fluorine gas (fluorination gas) with concentrations of substantially more than, in particular very much higher than 15% by volume or in particular than 20% by volume of elemental fluorine ($F_2$), especially of equal to much higher than 25% by volume (i.e., at least 25% by volume) of elemental fluorine ($F_2$), preferably of equal to much higher than 35% by volume or in particular than 45% by volume of elemental fluorine ($F_2$), is used for chemical synthesis, especially for the manufacture or for preparation of a fluorinated inorganic compound or fluorinated organic compound, respectively, as final products and/or intermediates, for usage in agro-, pharma-, electronics-, catalyst, solvent and other functional chemical applications.

Preferably, the present invention provides a fluorination process for the manufacture or preparation of a fluorinated inorganic compound or fluorinated organic compound, respectively, by direct fluorination using fluorine gas ($F_2$), by which it is possible to perform chemistry with $F_2$ as it comes directly out of the $F_2$-electrolysis reactors (fluorine cells).

More preferably, the present invention provides a fluorination process for the manufacture or preparation of a fluorinated inorganic compound or fluorinated organic compound, respectively, by direct fluorination using fluorine gas ($F_2$), by means of special equipment and special reactor design, for example, as described in FIG. 1 and FIG. 2 hereunder. The special equipment and special reactor design employed by the invention may comprise one or more packed bed towers, e.g., in the form of a gas scrubber system, or one or more microreactors. A packed bed towers, e.g., in the form of a gas scrubber system, may be preferred, more preferably a packed bed towers, e.g., in the form of an inverse gas scrubber system, used in a batch process as reactor.

The fluorination process for the manufacture or preparation of a fluorinated inorganic compound or fluorinated organic compound, respectively, by direct fluorination using fluorine gas ($F_2$), can be performed at suitable pressures, for examples at a pressure in the range of about 1 to about 25 bar (absolute), preferably at a pressure in a range of about 5 to about 20 bar (absolute), more preferably at a pressure in a range of about 10 to about 20 bar (absolute), and more preferably at a pressure in a range of about 15 to about 20 bar (absolute). In an example, the process is performed at a pressure of about 20 bar (absolute).

The fluorination process for the manufacture or preparation of a fluorinated inorganic compound or fluorinated organic compound, respectively, by direct fluorination using fluorine gas ($F_2$), can be performed at an approximately equimolar ratio of the inorganic starting compound or the organic starting compound, respectively, to the fluorination gas comprising highly concentrated $F_2$-gas. Preferably, the reaction is performed with a slight molar excess amount of the fluorination gas comprising highly concentrated $F_2$-gas.

Further, it has been discovered that despite the exothermic character of the direct fluorination reaction, e.g., within a given time period (e.g., less than 10 hours, or even less than 5 hours), the reaction of the invention can be performed as a larger scale reaction with high conversion rates, and without major impurities in the resulting fluorinated product. The fluorinated product can be produced in kilogram scale quantities, e.g., the direct fluorination process of the invention can be performed in a large-scale and/or industrial production of a fluorinated inorganic compound or fluorinated organic compound, respectively. For reason of calculating quantities, as an example but not intended to be limiting, reference is made to the larger scale reaction with high conversion rates of some example inorganic starting compounds or organic starting compounds, respectively; and resulting fluorinated inorganic compounds or fluorinated organic compounds, respectively; as displayed in the following table:

| Example | Quantity Kg (mol) | Reaction Time (h) | Yield (%) | Kg/h (mol/h) | Reactor Type |
|---|---|---|---|---|---|
| 1 | 4.0 (97.4 mol) | 5 | 96 | 0.8 (97.4 mol/h) | Column/Batch |
| 2 | 0.234 (5.7 mol) | 1 | 96 | 0.234 (5.7 mol/h) | Microreactor/Continuous |
| 7 | 0.017 (1 mol) | | | 0.017 (1 mol/h) | Microreactor/Continuous |
| 11 | 0.200 (1.51 mol) | 1 | 94 | 0.200 (1.51 mol/h) | Microreactor/Continuous |
| 13 | 0.4707 (2.8 mol) | 1 | 89 | 0.4707 (2.8 mol/h) | Microreactor/Continuous |
| 14 | 0.3999 (2.7 mol) | 1 | 79 | 0.3999 (2.7 mol/h) | Microreactor/Continuous |

Accordingly, it is preferred that the direct fluorination process of the invention is performed in a large-scale and/or industrial production of a fluorinated inorganic compound or fluorinated organic compound, respectively, e.g., in kilogram scale quantities, wherein in a batch process, or optionally in a continuous process, in a column reactor as described herein, e.g., in a time period of 1 h, at least about 0.1 kg of starting compound is fluorinated per hour, preferably at least about 0.3 kg or at least about 0.5 kg of starting compound, more preferably at least about 0.75 kg of starting compound, is fluorinated per hour, to yield a fluorinated inorganic compound or fluorinated organic compound, respectively, with a conversion of at least 75%, preferably about 80% conversion, more preferably about 85% conversion, and even more preferably about 95% conversion.

Accordingly, it is preferred that the direct fluorination process of the invention is performed in a large-scale and/or industrial production of a fluorinated inorganic compound or fluorinated organic compound, respectively, e.g., in a larger scale or even kilogram scale quantities, wherein in a microreactor process, in a continuous process, as described herein, e.g., in a time period of 1 h, at least about 0.5 mol/h starting compound, or at least about 1 mol/h starting compound, preferably at least about 1.5 mol/h starting compound, more preferably at least about 2 mol/h starting compound, even more preferably at least about 2.5 mol/h of starting compound, is fluorinated for a desired period of time (e.g., of at least 0.5 h, preferably of at least 1 h, more preferably of at least 2, 3, 4 or 5 h) to produce the required large-scale and/or industrial scale quantity of a fluorinated inorganic compound or fluorinated organic compound, respectively, a fluorinated inorganic compound or fluorinated organic compound, respectively, with a conversion of at least 75%, preferably about 80% conversion, more preferably about 85% conversion, and even more preferably about 95% conversion.

In a particular embodiment, it is preferred that the direct fluorination process of the invention is performed in a large-scale and/or industrial production of a fluorinated inorganic compound or fluorinated organic compound, respectively, e.g., in kilogram scale quantities, wherein in a microreactor process, in a continuous process, as described herein, the starting material, i.e., the inorganic starting compound or organic starting compound, respectively, is fluorinated for a desired period of time of at least about 1 h, preferably of at least about 2 h, more preferably of at least about 3 h, even more preferably of at least about 4 h, or most more preferably of at least about 5 h, or for even a longer time period that 5 h, to produce the required large-scale and/or industrial scale quantity of a fluorinated inorganic compound or fluorinated organic compound, respectively, with a conversion of at least 75%, preferably about 80% conversion, more preferably about 85% conversion, and even more preferably about 95% conversion.

Hence, in the said direct fluorination process of the invention performed in a large-scale and/or industrial production of a fluorinated inorganic compound or organic compound in a microreactor in a continuous process within e.g., in a time period of 1 h, approximate kilogram scale quantities of the starting material, i.e. an inorganic starting compound or organic starting compound, respectively, of at least about 0.015 kg or about 0.05 kg or about 0.1 kg or about 0.2 kg or about 0.3 kg, or of at least about 0.4 kg, or of at least about 0.5 kg, are fluorinated by direct fluorination according to the invention, to produce the required large-scale and/or industrial scale quantity of a fluorinated inorganic compound or fluorinated organic compound, respectively, with a conversion of at least 75%, preferably about 80% conversion, more preferably about 85% conversion, and even more preferably about 95% conversion.

The reaction is performed with an equimolar amount of highly concentrated $F_2$-gas, and, except for the reactions with deactivated benzene derivatives (see Examples 13 and 14; see further below), preferably in a slight molar excess amount of about 0.01 to about 0.5 mol/h, preferably of about 0.01 to about 0.4 mol/h or about 0.01 to about 0.3 mol/h, more preferably of about 0.01 to about 0.2 mol/h, most preferably of about 0.01 to about 0.1 mol/h, of highly concentrated $F_2$-gas.

If the fluorination is carried out in a solvent, then the direct fluorination according to the invention can be advantageously also performed using slightly sub-molar amounts of the fluorination gas comprising highly concentrated $F_2$-gas. This is particularly the case when deactivated benzene derivatives are used as the starting compound, as further described below.

The invention also relates to a use of a fluorination gas, wherein elemental fluorine ($F_2$) is present in a high concentration of substantially more than, in particular very much more than 15% by volume or in particular than 20% by volume, preferably equal to or more than 25% by volume (vol.-%), for the manufacture of a fluorinated inorganic compound or fluorinated organic compound, respectively, in a liquid medium comprising or consisting of an inorganic starting compound or an organic starting compound, respectively, wherein in the staring compound one or more hydrogen atoms are capable of being substituted by means of a halogenation reaction, preferably wherein the fluorine ($F_2$) is present in the fluorine containing gas in a high concentration in a range of from substantially more than, in particular very much more than 15 or 20 by volume (vol.-%) and up to 100% by volume, preferably equal to or more than 25 by volume (vol.-%) and up to 100% by volume (vol.-%); with a proviso that the starting compound, to be reacted with the fluorination gas, is not benzene, not benzoic acid, and not a benzoic acid derivative, and the fluorinated compound produced is not a fluorinated benzene, and in particular the fluorinated compound produced is not fluorobenzene or monofluorbenzene.

It is noted that the fluorination reaction of the present invention, in particular when carried out in the specific and/or preferred equipment or reactor designs as described by the present invention herein, can be already performed with concentrations of elemental fluorine ($F_2$) of 15% by volume or in particular than 20% by volume.

However, it is preferred that the fluorination reaction of the present invention, also when carried out in the specific and/or preferred equipment or reactor designs as described by the present invention herein, is performed with concentrations of elemental fluorine ($F_2$) at least 25% by volume, and more preferably with concentrations of elemental fluorine ($F_2$) of substantially more than 35% by volume or in particular substantially more than 45% by volume of elemental fluorine ($F_2$).

According to the present invention it is particularly preferred to perform the fluorination process for the manufacture or preparation of a fluorinated inorganic compound or fluorinated organic compound, respectively, by direct fluorination using fluorine gas ($F_2$), by which comes directly out of the $F_2$-electrolysis reactors (fluorine cells). Such electrolysis fluorine gas ($F_2$) normally has a concentration of about 97% elemental fluorine ($F_2$).

The electrolysis fluorine gas ($F_2$) normally having a concentration of about 97% elemental fluorine ($F_2$) can be used without purification as it is derived from the $F_2$-electrolysis reactors (fluorine cells), or if desired, it may be purified.

Further, the electrolysis fluorine gas ($F_2$) normally having a concentration of about 97% by volume (vol.-%) of elemental fluorine ($F_2$) can be used in the in the such concentration as it is derived from the $F_2$-electrolysis reactors (fluorine cells), or optionally it may be diluted by an inert gas, preferably nitrogen ($N_2$), to a desired concentration of at least 80% by volume (vol.-%) of elemental fluorine ($F_2$). More preferably the electrolysis fluorine gas ($F_2$) is only diluted, if desired, by no more than 15% by volume (vol.-%), no more than 10% by volume (vol.-%), and most preferably by no more that 5% by volume (vol.-%), of an inert gas, preferably nitrogen ($N_2$).

Surprisingly it was also found that the use of inert gas in larger ratios of inert gas to elemental fluorine has disadvantages in terms of process controllability of the fluorination reaction, for example, in terms of effective mixing of the elemental fluorine with the liquid compound to be fluorinated, heat transfer control, e.g., poor heat exchange, and maintenance of desired reaction conditions in the microenvironments in the reaction mixture. These disadvantages equally apply in bed tower reactor (gas scrubber system) technology and in microbubble microreactor or comparable continuous flow technology. For example, in a coil reactor or microreactor, at high inert gas concentrations, e.g., low fluorine (F2) concentrations, in addition to the poor heat exchange, there are also ineffective (reaction) zones with (inert) gas bubbles, which nullifies the advantages of using a coil reactor or a microreactor, and the same is observed in bed tower reactor (gas scrubber system) technology.

Definitions

Direct Fluorination: Introducing one or more fluorine atoms into a compound by chemically reacting a starting compound, e.g. according to the present invention an inorganic starting compound or organic starting compound, respectively, with elemental fluorine ($F_2$) such that one or more fluorine atoms are covalently bound into the fluorinated inorganic compound or organic compound, respectively.

Compound: A molecule composed of at least two atoms bound by covalent binding. In the molecule, often also called substance, the atoms are covalently linked together to form a self-contained, chemical formation. A molecule defined in this way is the smallest particle of a certain pure substance and has a determinable molecular mass, wherein the atoms are held together by chemical bonds and are at least as long stable that they can be observed, for example, at least spectroscopically. A molecule or substance defined in this way is the smallest part of a certain pure substance and has a determinable molecular mass, and other determinable physiochemical properties. Here, in the invention, for example, the starting compound is a compound provided to be reacted with elemental fluorine ($F_2$). The starting compound may be an inorganic molecule (i.e. no salt) as inorganic starting compound, or an organic compound, respectively. The compound obtained by the process of the invention, for example, may be a fluorinated inorganic compound or a fluorinated organic compound, respectively. However, for the purpose of this invention, benzene is expressively excluded from the group of organic starting compounds, and fluorinated benzene, fluorobenzene or monofluorobenzene is expressively excluded from the group of fluorinated organic compounds to be produced.

Inorganic Chemistry is the chemistry of all carbon-free compounds and some exceptions, i.e., it is the chemistry related to inorganic substances or inorganic compounds. Inorganic substances or compounds traditionally include the elements and all compounds that do not contain carbon. There are some exceptions to carbon compounds, which are built up just like typical inorganic substances or historically assigned to inorganic compounds. These include the hydrogen-free chalcogenides of carbon (carbon monoxide, carbon dioxide, carbondisulfide), carbonic acid and carbonates, carbides and ionic cyanides, cyanates and thiocyanates. The hydrocyanic acid is considered a borderline case and is treated both in the organic and inorganic. Although traditionally classified as inorganic chemistry, it may be considered to be a nitrile (organic group) of formic acid.

Organic chemistry (organics) is a branch of chemistry which covers the chemical compounds based on carbon, with some exceptions such as some inorganic carbon compounds and elemental (pure) carbon; see for example also here before exceptions and borderline cases mentioned in the description of inorganic chemistry. With few exceptions, organic chemistry encompasses the chemistry of all compounds that carbon enters into with itself and other elements. This also includes all the building blocks of the currently known life. The exceptions formally concern first the elemental forms of carbon (graphite, diamond) and, systematically, all non-hydrogen-containing chalcogenides of carbon (carbon monoxide, carbon dioxide, carbondisulfide), carbonic acid and carbonates, carbides and ionic cyanides, cyanates and thiocyanates (see carbon compounds).

Hydrocyanic acid belongs to the borderland of inorganic and organic chemistry. Although traditionally classified as inorganic chemistry, it is considered to be a nitrile (organic group) of formic acid. The cyanides are treated in the inorganic, which here only the salts of hydrogen cyanide are meant, whereas the esters of hydrocyanic acid known under the same name belong as nitriles to the organics. The cyanic acids, thiocyanic acids and their esters are also considered as borderline cases.

Further, the organometallic chemistry (metal organyls) is not specifically attributed to organic or inorganic chemistry. In the context of the present invention, organometallic chemistry (metal organyls) is not encompassed by the meanings of both, the organic chemistry or inorganic chemistry, or by the meaning of organic compound or inorganic compound.

The term "deactivated benzene derivative" denotes a substituted benzene (C6-aromatic systems) bearing an electron withdrawing and releasing group. For example, such deactivating group (an electron withdrawing and releasing group) can be a nitro group ($NO_2$), a nitrile group (CN), a hydroxyl group (OH), an O-methyl group ($OCH_3$), an aldehyde group (CHO). There may be one to three of such deactivating groups (an electron withdrawing and releasing groups) bonded to the benzene ring. For the purpose of this invention it is expressively noted that benzene itself is not regarded as a deactivated compound, and that benzoic acid, and benzoic acid derivatives are expressively not comprised by the term "deactivated benzene derivative". Hence, in the context of the present invention there is the proviso that the starting compound in the present invention is not benzene, not benzoic acid, and not a benzoic acid derivative, The term "liquid medium" may mean a solvent which inert to fluorination under the reaction conditions of the direct fluorination, in which the starting compound and/or fluorinated target compound may be dissolved, and/or the starting compound itself may be a liquid serving itself as liquid medium, and in which the fluorinated target compound may be dissolved if it is not a liquid, or if it is a liquid may also serve as the liquid medium.

The numerical ranges disclosed herein include all values from, and including, the lower and upper value. For ranges containing explicit values (e.g., 1 to 7), any subrange between any two explicit values is included (e.g., 1 to 2; 2 to 6; 5 to 7; 3 to 7; 5 to 6; etc.).

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

The term "vol.-%" as used herein means "% by volume". Unless otherwise stated, all percentages (%) as used herein denote "vol.-%" or "% by volume", respectively.

For example, the use of the term "essentially", in referring to a fluorination gas consisting essentially of $F_2$-gas as it directly comes out of the $F_2$-electrolysis reactors (fluorine cells), means that providing such $F_2$-gas does not involve major purification and/or providing another gas, e.g., an inert gas, separate and/or in admixture in amounts and/or under conditions that would be sufficient to provide a change in the composition of an $F_2$-gas as produced in and as it is withdrawn as gaseous product from $F_2$-electrolysis reactors (fluorine cells) of more than about ±5% by volume, or preferably of more than about ±3% by volume. Accordingly, such a fluorination gas consisting essentially of $F_2$-gas as it directly comes out of the $F_2$-electrolysis reactors (fluorine cells) is meant to comprise elemental fluorine ($F_2$) in a concentration of at least about 92% by volume, or preferably of at least about 95% by volume. Especially, such a fluorination gas consisting essentially of $F_2$-gas as it directly comes out of the $F_2$-electrolysis reactors (fluorine cells) may comprise elemental fluorine ($F_2$) in a concentration in a range of about 92-100% by volume, or preferably in a range of about 95-100% by volume, or more preferably in a range of in a range of about 92-99% by volume, or preferably in a range of about 95-99% by volume, or in a range of in a range of about 92 to about 97% by volume, or preferably in a range of about 95 to about 97% by volume.

The numerical ranges disclosed herein include all values from, and including, the lower and upper value. For ranges containing explicit values (e.g., 1 to 7), any subrange between any two explicit values is included (e.g., 1 to 2; 2 to 6; 5 to 7; 3 to 7; 5 to 6; etc.).

DESCRIPTION OF THE PREFERRED EMBODIMENTS

Figure 1:
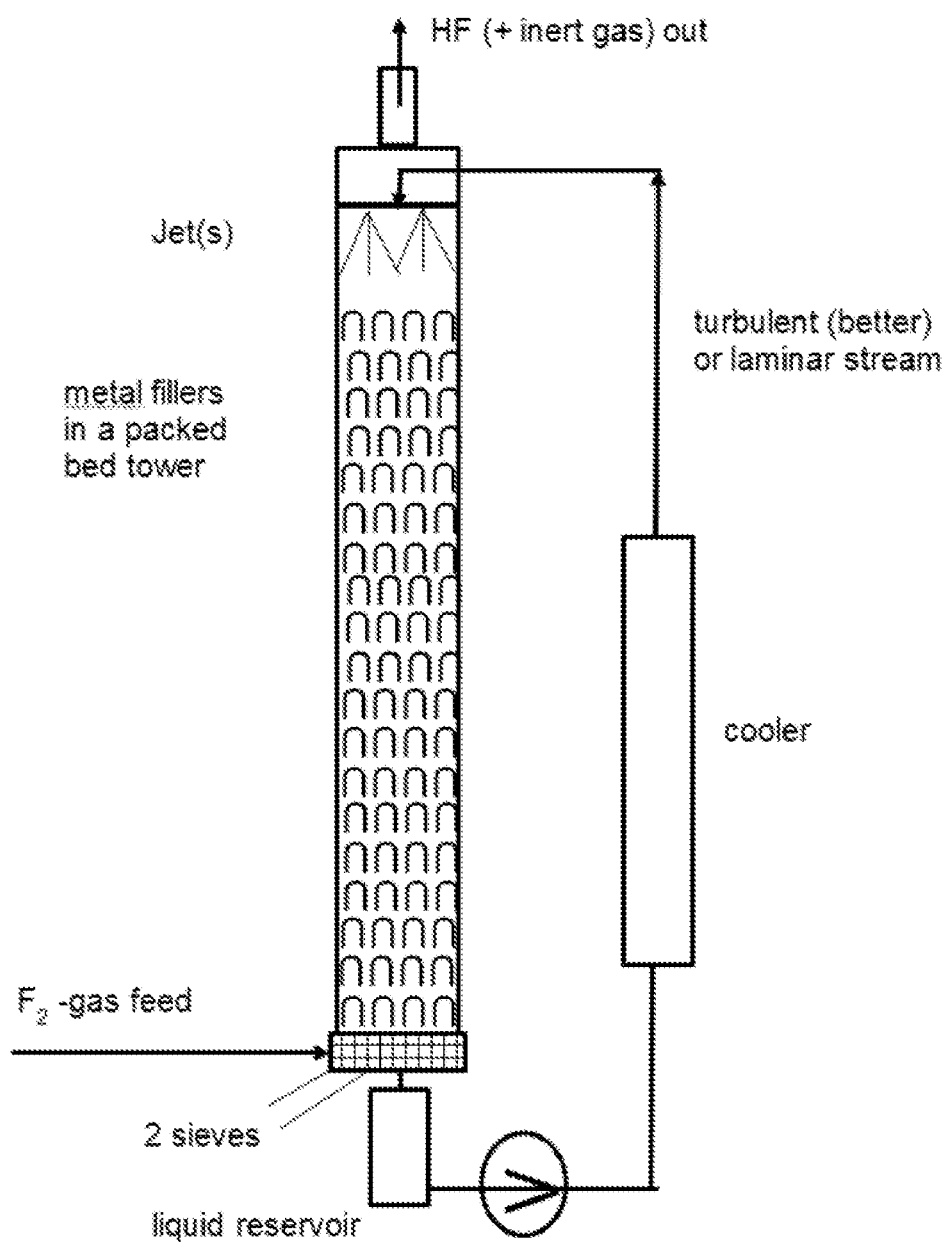
FIG. 1 shows fluorination using a gas scrubber system.

As briefly described in the Summary of the Invention, and defined in the claims and further detailed by the following description and examples herein, the invention is particularly making use of a fluorination gas, wherein the elemental fluorine ($F_2$) is present in a high concentration, and to a process for the manufacture of a fluorinated inorganic compound or a fluorinated organic compound, respectively, by direct fluorination employing a fluorination gas, wherein the elemental fluorine ($F_2$) is present in a high concentration.

The invention makes use of a fluorination gas, wherein the elemental fluorine ($F_2$) is present in a high concentration, for example, in a concentration of elemental fluorine ($F_2$) especially of equal to much higher than 15% or 20% by volume (i.e., at least 15% or 20% by volume), and preferably at least 25% by volume, to a process for the manufacture of a fluorinated inorganic compound or a fluorinated organic compound, respectively, by direct fluorination employing a fluorination gas, wherein the elemental fluorine ($F_2$) is present in a high concentration. The process of the invention is directed to the manufacture of a fluorinated inorganic compound or a fluorinated organic compound, respectively, by direct fluorination, especially is of interest in the manufacture or preparation of a fluorinated inorganic compound or a fluorinated organic compound, respectively, as final products and as well intermediates, for usage in agro-, pharma-, electronics-, catalyst, solvent and other functional chemical applications. The fluorination process of the invention may be performed batch-wise or in a continuous manner. If the process of the invention is performed batch-wise, a column (tower) reactor may be used. If the process of the invention is continuous a microreactor may be used. If desired, it is also possible to perform the process of the invention continuously in a column (tower) reactor (gas scrubber system). However, it is preferred to perform a continuous process of the invention in a microreactor.

Especially, in one aspect the invention is directed to the use of a fluorination gas, wherein elemental fluorine ($F_2$) is present in a high concentration of substantially more than, in particular very much more than at least 10% by volume of elemental fluorine ($F_2$), especially of equal to much higher than 15% or 20% by volume (i.e., at least 15% or 20% by volume), and preferably at least 25% by volume, for the manufacture of a fluorinated inorganic compound or a fluorinated organic compound, respectively, in a liquid medium comprising or consisting of a starting compound having one or more hydrogen atoms that are capable of being substituted by means of a halogenation reaction, preferably wherein the fluorine ($F_2$) is present in the fluorine containing gas in a high concentration in a range of from substantially more than, in particular very much more than 15% or 20% by volume (i.e., at least 15% or 20% by volume), and preferably at least 20% by volume, each up to 100% by volume, preferably equal to or more than 25% by volume and up to 100% by volume (vol.-%).

In this invention it now was found that, preferably in special equipment and with special reactor design such as, e.g., a microreactor or a packed bed tower (preferably made of Hastelloy), especially a packed bed tower containing fillers, e.g., metal fillers (e.g. Hastelloy) or plastic fillers, preferably wherein the tower (e.g., made out of Hastelloy) is filled either with E-TFE or metal fillings (Hastelloy), for example each of about 10 mm diameter as available from Raschig (http://www.raschig.de/Fllkrper). The type of fillings is quite flexible, Raschigs Pall-Rings made out of Hastelloy can be used, and advantageously E-TFE-fillings.

In the said special equipment and with special reactor design such as, e.g., a microreactor or a packed bed tower (preferably made of Hastelloy), a fluorine gas with concentrations of substantially more than, in particular very much higher than 15% or 20% by volume of elemental fluorine ($F_2$), especially of equal to much higher than 20% by volume (i.e., at least 20% by volume) of elemental fluorine ($F_2$), preferably of equal to much higher than 25% by volume of elemental fluorine ($F_2$), can be used for chemical synthesis especially for the preparation of a fluorinated inorganic compound or a fluorinated organic compound, respectively, as final products and/or intermediates, for usage in agro-, pharma-, electronics-, catalyst, solvent and other functional chemical applications. This invention allows fluorination chemistry with $F_2$ gas with concentrations preferably equal to substantially more than, in particular very much higher than 25% by volume of elemental fluorine ($F_2$). In a applying the present fluorination process it is possible to perform chemistry with $F_2$ as it comes directly out of the $F_2$-electrolysis reactors (fluorine cells). A representative composition of fluorine gas produced by a fluorine cell is 97% $F_2$, up to 3% $CF_4$ (formed from damage of the electrodes), for example, traces of HF, $NO_2$, $OF_2$, $COF_2$, each % by volume and based on the total volume of the fluorine containing gas as 100% by volume. Regarding the scope of the present invention it is to be noted that, that for legal reason only but not for technical reason, there is a proviso that the starting compound, to be reacted with the fluorination gas, is not benzene, not benzoic acid, and not a benzoic acid derivative, and the fluorinated compound produced is not a fluorinated benzene, and in particular the fluorinated compound produced is not fluorobenzene or monofluorbenzene.

In the fluorination gas the elemental fluorine ($F_2$) may be diluted by an inert gas. The inert gas then constitutes the substantial difference (e.g., there may be only minor quantities of by-products (e.g., $CF_4$) of no more than about 5% by volume, preferably of no more than about 3% by volume, and only traces impurities (e.g., such like HF, $NO_2$, $OF_2$, $COF_2$), in the fluorination gas).

An inert gas is a gas that does not undergo chemical reactions under a set of given conditions.

The noble gases often do not react with many substances and were historically referred to as the inert gases. Inert gases are used generally to avoid unwanted chemical reactions degrading a sample. These undesirable chemical reactions are often oxidation and hydrolysis reactions with the oxygen and moisture in air.

Typical inert gases are noble gases, and the very common inert gas nitrogen ($N_2$). The noble gases (historically also the inert gases; sometimes referred to as aerogens) make up a group of chemical elements with similar properties; under standard conditions, they are all odorless, colorless, monatomic gases with very low chemical reactivity. The six noble gases that occur naturally are helium (He), neon (Ne), argon (Ar), krypton (Kr), xenon (Xe), and the radioactive radon (Rn).

Purified argon and nitrogen gases are most commonly used as inert gases due to their high natural abundance (78.3% N2, 1% Ar in air) and low relative cost. The preferred is nitrogen ($N_2$) as the inert gas for diluting the elemental fluorine ($F_2$) in the fluorination gas to the desired but still high concentration, as defined herein.

Preferred is a fluorination gas, wherein the elemental fluorine ($F_2$) is diluted by nitrogen ($N_2$). An example composition of a fluorination gas, using nitrogen ($N_2$) as the inert gas, is as follows (here as purified composition (fluorine-nitrogen gas mixture) as filled in a steel gas cylinder):

| Molecular Formula: $F_2$<br>Item | Molecular Weight: 38<br>Index |
|---|---|
| $F_2$ content (volume fraction)/$10^{-2}$ | 20 |
| $N_2$ content (volume fraction)/$10^{-2}$ | 80 |
| $O_2$ content (volume fraction)/$10^{-2}$ | ≤0.08 |
| $CF_4$ content (volume fraction)/$10^{-2}$ | ≤0.03 |
| HF content (volume fraction)/$10^{-2}$ | ≤0.50 |

Properties: melting point: −218° C., boiling point: −187° C., relative densitiy (moisture = 1) 1.14 (−200° C.), soluble in water, relative density (air = 1) 1.70, saturated vapor pressure (kpa): 101.32 (−187° C.), critical pressure (MPA): 5.57.

Figure 2:
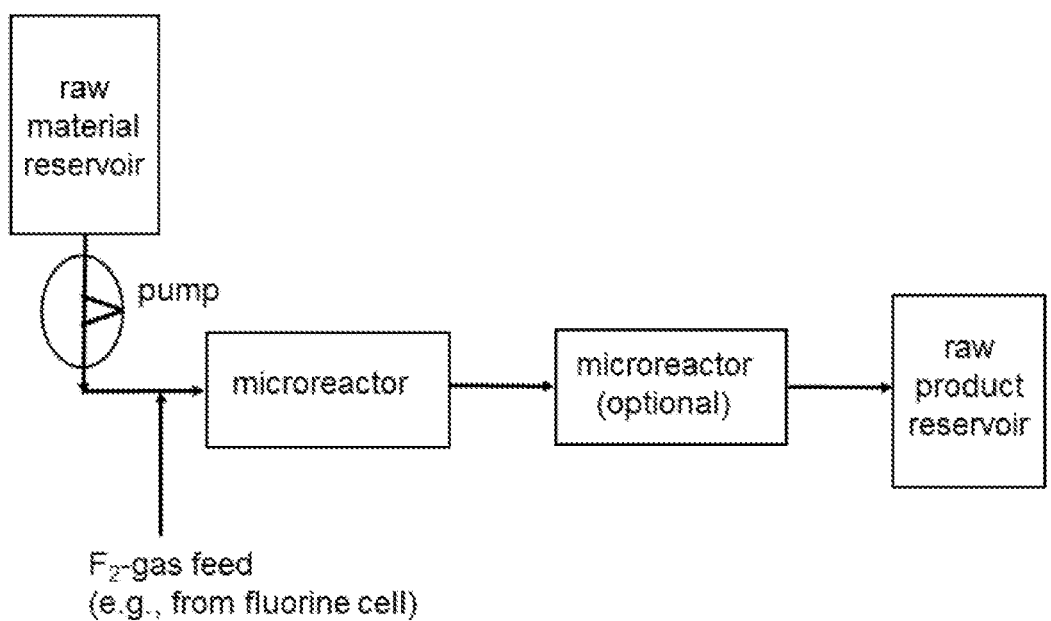
FIG. 2 shows continuous fluorination in a one or several microreactor (in series) system.

The following two FIGS. 1 and 2 illustrate the industrial options to use $F_2$ gas with little or even with no dilution with inert gas:

FIG. 1: Fluorination using a gas scrubber system.

Batch fluorination with highly concentrated $F_2$ gas in a counter-current system (the reservoir is containing the liquid raw material or optionally the raw material in an inert solvent). If highly concentrated $F_2$ is used together with some inert gas (e.g. 10% $N_2$) the pressure during the fluorination is kept at 20 bar by a pressure valve. The inert gas together with (only) some HF leaves as purge gas during reaction.

FIG. 2: Continuous fluorination in a one or several microreactor (in series) system.

The raw material reservoir still contains the equimolar formed HF. This can be subjected a batch or continuous distillation or if a solvent is present, after removal of the solvent and HF a re-crystallization for purification. Spray drying is another option depending on the product properties. A second or even more microreactor in series is just for the purpose of extending the residence time if needed.

For example, the following compounds or intermediates can be used as starting compound (inorganic or organic, respectively) or be prepared according to this invention (by way of example only, i.e., non-exhaustive) as indicated in the following schemes:

Scheme 1

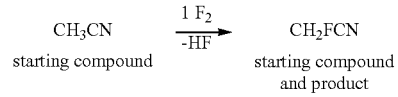

-continued

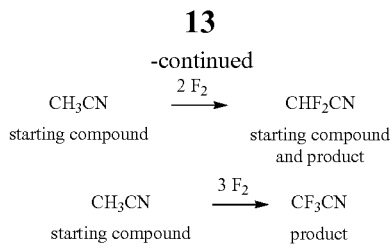

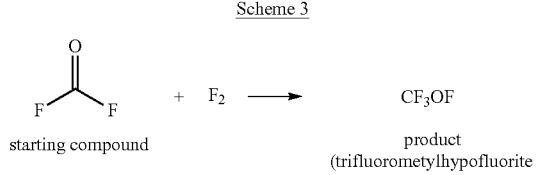

The fluorination product trifluoroacetonitrile (CF$_3$CN) can be used as raw material to prepare a conducting salt for lithium ion batteries.

However, regarding the scope of the present invention it is to be noted that, that for legal reason only but not for technical reason, there is a proviso that the use of trifluoroacetonitrile (CF$_3$CN) in the manufacture of a conducting salt for lithium ion batteries, any process for the manufacture of a conducting salt for lithium ion batteries derived from trifluoroacetonitrile (CF$_3$CN), and the conducting salt for lithium ion batteries itself derived from such use or manufacture including in at least one step trifluoroacetonitrile (CF$_3$CN), is excluded from the scope of the present invention. The scope of the present invention, therefore, is limited to the manufacture of trifluoroacetonitrile (CF$_3$CN) by direct fluorination with a fluorination gas comprising or consisting of a highly concentrated F$_2$-gas.

CF$_3$OF (trifluoromethylhypofluorite) is a fluorinating reagent for the production of polyfluoroether as "functional fluids", e.g. EP0267627 A1 (Ausimont). CF$_3$OF (trifluoromethylhypofluorite) is also useful for the production of SF$_4$ (also already described by Roger et al. in Journal of the American Chemical Society Volume 79, 1957, 5625-5627) a fluorinating agent to convert OH-groups to F or Carbonyl groups to CF$_2$ under mild conditions. Another industrially very important usage of CF$_3$OF according to present invention is the application in production of highest purity LiF (out of Li$_2$CO$_3$) which is used for Li-battery conducting salt and other applications in electronics (see Roger et al. JACS reference cited here above): CF$_3$OF+2 Li$_2$CO$_3$=>3 CO$_2$+4 LiF+0.5 O$_2$.

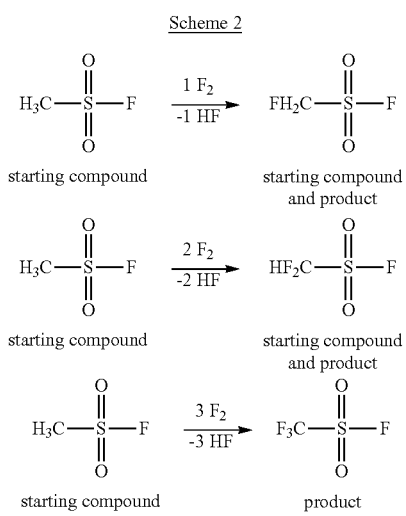

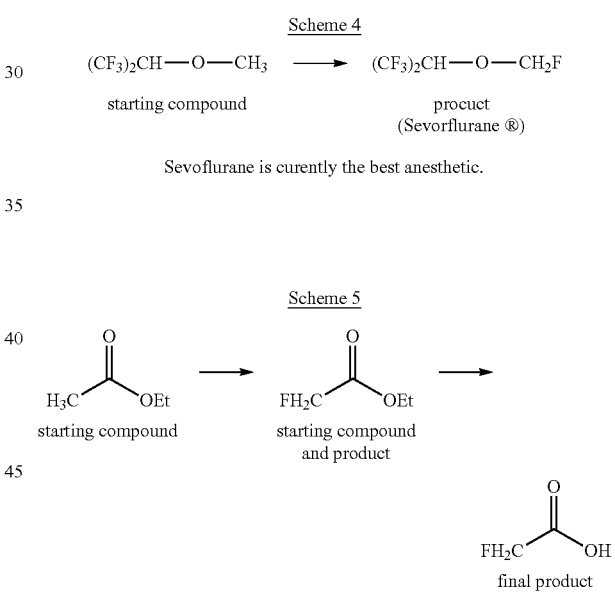

The fluorination product trifluorosulfonylfluoride (CF$_3$SO$_2$F) can be used as raw material to prepare a conducting salt for lithium ion batteries.

However, regarding the scope of the present invention it is to be noted that, that for legal reason only but not for technical reason, there is a proviso that the use of trifluorosulfonylfluoride (CF$_3$SO$_2$F) in the manufacture of a conducting salt for lithium ion batteries, any process for the manufacture of a conducting salt for lithium ion batteries derived from trifluorosulfonylfluoride (CF$_3$SO$_2$F), and the conducting salt for lithium ion batteries itself derived from such use or manufacture including in at least one step trifluorosulfonylfluoride (CF$_3$SO$_2$F), is excluded from the scope of the present invention. The scope of the present invention, therefore, is limited to the manufacture of trifluorosulfonylfluoride (CF$_3$SO$_2$F) by direct fluorination with a fluorination gas comprising or consisting of a highly concentrated F$_2$-gas.

Monofluoro acetic acid is a monofluorine building block and the sodium monofluoro acetate is an active ingredient for agro-chemicals. Of course, monofluoro acetic acid can also be prepared from the monofluoro acetonitrile.

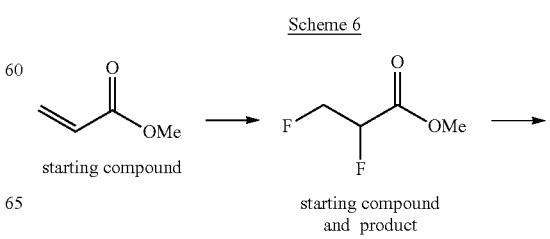

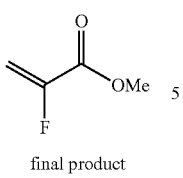

final product

The fluoroacrylate is the raw material for the Patiromer® (preparation for renal patients) of Relypsa, see U.S. Pat. No. 9,061,990. This reaction has been described in the microreactor (EP2664607), but only with diluted fluorine.

Scheme 7

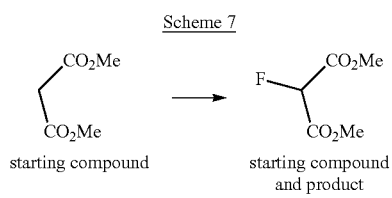 [SMILES: COC(=O)CC(=O)OC ; COC(=O)C(F)C(=O)OC]

Fluoromalonic ester production with $F_2$ is known, but only with diluted fluorine. Fluoromalonic ester is a key building block for an active ingredient for agro-chemicals.

Scheme 8

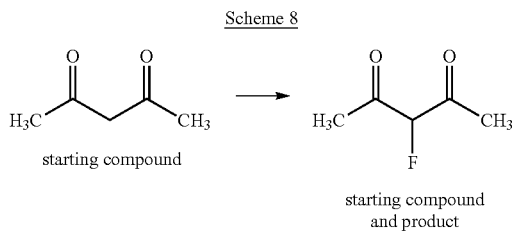

Fluorination of many 1,3-dicarbonyl methylene compounds; in principle all reactions listed in WO 95/14646 are possible, too, to be performed by the present invention like fluorinated acetyl acetone, fluorinated acetoacetates as well as fluorinated cyclic cyclopentanoneand cyclohexanone derivatives, especially for example, to provide following products:

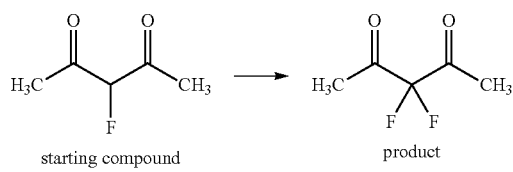

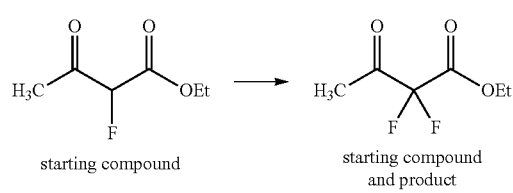

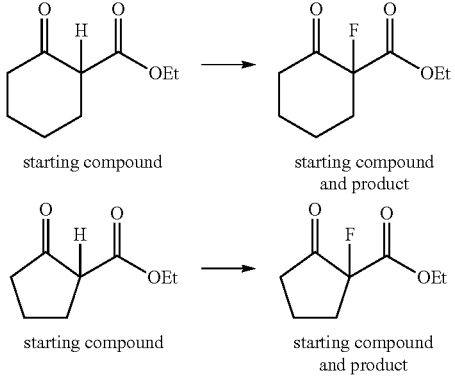

In 2-position fluorinated acetacetates and cyclohexanone acetates and Cyclopentanone acetates can be used as starting material for producing monofluoroacetones, difluoroacetones, and monofluorocyclohexanone and monofluorocyclopentanone after transesterification/decarboxylation prepared according to the principle disclosed in EP623577.

If hexafluoroacetylacetone or trifluoroacetylacetone is used as starting material the perfluorinatedoctofluoroacetylacetone might have application in electronics industries like additives for batteries; this example is not given in previously mentioned WO 95/14646.

Important compounds are also:

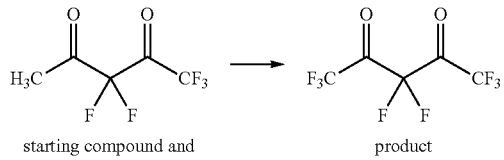

product

The mentioned perfluorinatedoctafluoroacetylacetone can alternatively be prepared by fluorinating acetylacetone with 8 equivalents of $F_2$ according to this invention.

Scheme 9

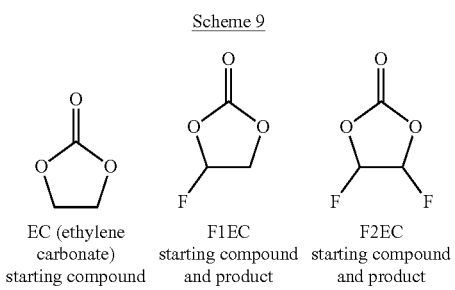

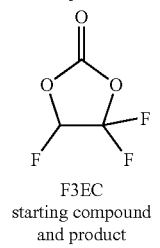

F3EC
starting compound
and product

These (also multiply) fluorinated ethylene carbonates can all be made from ethylene carbonate (EC), but with altered $F_2$ stoichiometry.

Scheme 10

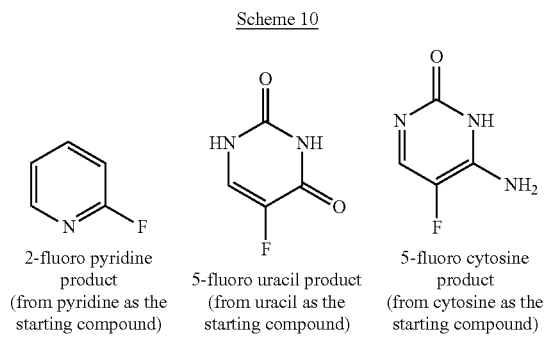 [SMILES: Fc1ccccn1 ; O=c1[nH]cc(F)c(=O)[nH]1 ; Nc1[nH]c(=O)ncc1F]

2-fluoro pyridine product (from pyridine as the starting compound)

5-fluoro uracil product (from uracil as the starting compound)

5-fluoro cytosine product (from cytosine as the starting compound)

Scheme 11

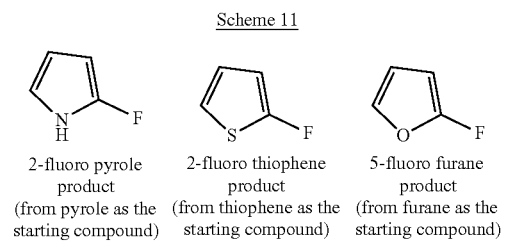 [SMILES: Fc1ccc[nH]1 ; Fc1cccs1 ; Fc1ccco1]

2-fluoro pyrole product (from pyrole as the starting compound)

2-fluoro thiophene product (from thiophene as the starting compound)

5-fluoro furane product (from furane as the starting compound)

5-membered heterocycles are described in Gazzettachimicaitaliana 120 (12) (1990), pp. 749. There deep temperatures and low(er) selectivities are mentioned. In contrary to this work, the process of this invention in a microreactor delivers with 95% selectivity the 2-Fluorothiophene and only traces of the 3-fluoro thiophene, the fluorination allows higher temperatures at 5–10° C. for the reaction compared to –63° C. in known procedure. Similar result can be obtained with N-methylpyrrole giving mainly the 3-fluoro-N-methylpyrrole.

Also, in contrary to the known chemistry giving 1,4-difluorinated product, conversion of furane with $F_2$ at 5° C. in a microreactor in the framework of this invention gives 2-fluorofurane with 81% yield.

Scheme 12

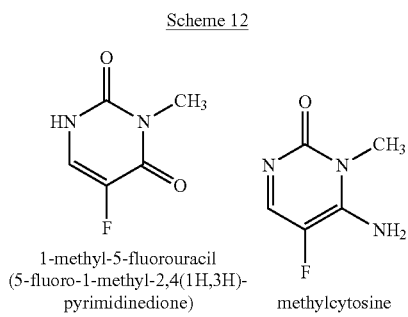

1-methyl-5-fluorouracil (5-fluoro-1-methyl-2,4(1H,3H)-pyrimidinedione)

methylcytosine

The 1-methyl-5-fluorouracil (5-fluoro-1-methyl-2,4(1H,3H)-pyrimidinedione) as 5-fluorouracil derivative can be prepared out of 1-methyluracil and the 5-fluoro-3-methylcytosine as a cytosine derivative can be prepared directly out of 3-methylcytosine by direct fluorination according to this invention instead of a more complicated methylation reaction out of the 5-fluorouracil as described by Kuz'menko, I. I.; et al ZhurnalObshcheiKhimii (1989), 59(8), 1751-5 for the fluoromethyluracil and described in WO 2013/025795 for the preparation of 5-fluoro-3-methylcytosine even applying a kind of sophisticated protecting group chemistry, this also avoids usage of $CF_3OF$ which would require two more chemical steps.

A particular compound that may be obtained by the process of the present invention is the compound fluorocyanide (F—CN), preferably fluorocyanide (F—CN) obtainable or obtained by a process according to any of the process embodiments of the invention, in situ or in isolated form.

The said compound of fluorocyanide (F—CN), i.e., as produced according to the process of this invention, is novel and is provided for the first time by the present invention in excellent purity. Accordingly, in this aspect the invention is also directed to the compound of fluorocyanide (F—CN), preferably fluorocyanide (F—CN) obtainable or obtained by a process according to any of the process embodiments of the invention, in situ or in isolated form.

The fluorination product fluorocyanide (F—CN) can be used as raw material to prepare a conducting salt for lithium ion batteries.

However, regarding the scope of the present invention it is to be noted that, that for legal reason only but not for technical reason, there is a proviso that the use of fluorocyanide (F—CN) in the manufacture of a conducting salt for lithium ion batteries, any process for the manufacture of a conducting salt for lithium ion batteries derived from fluorocyanide (F—CN), and the conducting salt for lithium ion batteries itself derived from such use or manufacture including in at least one step fluorocyanide (F—CN), is excluded from the scope of the present invention. The scope of the present invention, therefore, is limited to the manufacture of fluorocyanide (F—CN) by direct fluorination with a fluorination gas comprising or consisting of a highly concentrated $F_2$-gas.

Fluorination of Deactivated Benzene Derivatives:

According to the present invention it is also possible to fluorinate deactivated benzene derivatives by the direct fluorination process as defined herein using, in contrast to Chambers et al. (see supra), a fluorination gas comprising or consisting of highly concentrated elemental fluorine ($F_2$). Examples for such direct fluorinations, according to the invention, of deactivated benzene derivatives are given hereunder in Schemes 13 and 14. The definition of "deactivated benzene derivatives" is given further above. It is to be noted that benzene itself is not regarded as a "deactivated" compound.

These direct fluorination reactions may be performed in a solvent which is inert to fluorination under the reaction conditions, for example, the solvent may be acetonitrile ($CH_3CN$). It is noted that the benzene ring of the deactivated benzene derivatives has a higher reactivity than the solvent, e.g., acetonitrile, regarding the direct fluorination reaction.

In such a case, wherein the fluorination is carried out in a solvent, then the direct fluorination according to the invention is advantageously performed using slightly submolar amounts of the fluorination gas comprising highly concentrated $F_2$-gas. This is particularly the case when deactivated benzene derivatives are used as the starting compound, as further described below, for the starting compounds in Schemes 13 and 14 are solids, and therefore, a solvent (acetonitrile) is used.

Further, it has been discovered that despite the exothermic character of the direct fluorination reaction, e.g., within a given time period (e.g., less than 10 hours, or even less than 5 hours), the reaction of the invention can be performed as a larger scale reaction with high conversion rates, and without major impurities in the resulting fluorinated product. The fluorinated product can be produced in kilogram scale quantities, e.g., the direct fluorination process of the invention can be performed in a large-scale and/or industrial production of a fluorinated deactivated benzene compound. For reason of calculating quantities, as an example but not intended to be limiting, reference is made to the molecular weight of 1,3-dinitro-benzene of 168.11 g/mol, and of fluoro-1,3-dinitro-benzene of 186.10 g/mol (see Example 13); and to 3-nitro-benzonitrile of 148.12 g/mol, and of 3-fluoro-5-nitro-benzonitrile of 168.11 g/mol (see Example 14).

Accordingly, it is preferred that the direct fluorination process of the invention is performed in a large-scale and/or industrial production of a fluorinated deactivated benzene compound, e.g., in kilogram scale quantities, wherein at least about 0.1 kg/h of deactivated benzene compound as the starting material is fluorinated per hour, preferably at least about 0.3 kg/h of deactivated benzene as the starting material is fluorinated per hour, to yield a fluorinated deactivated benzene compound, with a conversion of at least 70%, preferably about at least 75% or even at least 85% conversion; and/or with a product yield of at least 70%, preferably about at least 75% or even at least 85%.

Accordingly, it is preferred that the direct fluorination process of the invention is performed in a large-scale and/or industrial production of a fluorinated deactivated benzene compound, e.g., in a larger scale or even kilogram scale quantities, e.g., within a given time period, wherein in a microreactor process, in a continuous process, as described herein, at least about 0.5 mol/h deactivated benzene compound, or at least about 1 mol/h, preferably at least about 2 mol/h, more preferably at least about 2.5 mol/h or 3 mol/h, of a deactivated benzene compound as the starting material is fluorinated for a desired period of time (e.g., of at least 0.5 h, preferably of at least 1 h, more preferably of at least 2, 3, or 4 h) to produce the required large-scale and/or industrial scale quantity of fluorinated deactivated benzene compound, with a conversion of at least 70%, preferably about at least 75% or even at least 85% conversion; and/or with a product yield of at least 70%, preferably about at least 75% or even at least 85%.

The reaction is performed with an equimolar amount of highly concentrated $F_2$-gas, and optionally in a slight molar excess amount of about 0.01 to about 0.1 mol/h, but preferably in a slight sub-molar amount of about −0.01 to about 0.1 mol/h, more preferably in a slight sub-molar amount of about −0.02 to about −0.09 mol/h, even more preferably of about −0.03 to about −0.08 mol/h, most preferably of about −0.5 to about −0.07 mol/h, of highly concentrated $F_2$-gas.

Scheme 13

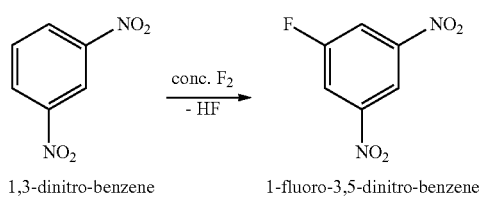

1,3-dinitro-benzene    1-fluoro-3,5-dinitro-benzene

A fluoro-dinitro-benzene is described for the use in cancer therapy (U.S. Pat. No. 5,290,551), in CN 1360888 the use for skin diseases is claimed.

Scheme 14

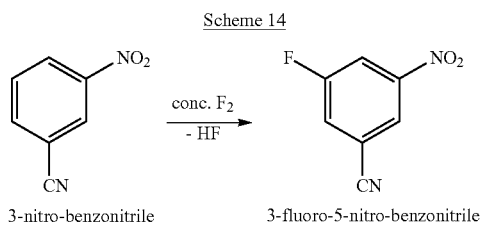 [SMILES: N#Cc1cccc([N+](=O)[O-])c1 ; "- HF" ; N#Cc1cc(F)cc([N+](=O)[O-])c1]

3-nitro-benzonitrile    3-fluoro-5-nitro-benzonitrile

The 3-fluoro-5-nitro-benzonitrile is claimed when used against AIDs (see, e.g., WO 2018/002848).

Fluorination with Fluorination Gas Containing Elemental Fluorine in a High Concentration:

As briefly described, and defined in the claims and further detailed by the following description and examples herein, the invention is particularly directed to a use of a fluorination gas, wherein the elemental fluorine ($F_2$) is present in a high concentration, and to a process for the manufacture of a fluorinated inorganic compound or fluorinated organic compound, respectively, by direct fluorination employing a fluorination gas, wherein the elemental fluorine ($F_2$) is present in a high concentration. This particular aspect of the invention shall be further explained herein after.

As shown in the examples, the direct fluorination can be performed already with a fluorination gas, based on the total fluorination gas composition as 100% by volume, comprising at least 20% by volume of elemental fluorine ($F_2$) and up to about 80% by volume of an inert gas, preferably nitrogen ($N_2$), for example, the composition of a fluorination gas, using nitrogen ($N_2$) as the inert gas, as described above as purified composition fluorine-nitrogen gas mixture as filled in a steel gas cylinder.

By the present invention it was found that the fluorination process according to the invention is already feasible with a fluorination gas, based on the total fluorination gas composition as 100% by volume, comprising at least 20% by volume of elemental fluorine ($F_2$), but for an industrial process undesirably low conversion rates of only about up to 30 to 45% are achieved.

Surprisingly it was also found that the use of inert gas in larger ratios of inert gas to elemental fluorine has disadvantages in terms of process controllability of the fluorination reaction, for example, in terms of effective mixing of the elemental fluorine with the liquid compound to be fluorinated, heat transfer control, e.g., poor heat exchange, and maintenance of desired reaction conditions in the microenvironments in the reaction mixture. These disadvantages equally apply in bed tower reactor (gas scrubber system) technology and in microbubble microreactor or comparable continuous flow technology. For example, in a coil reactor or microreactor, at high inert gas concentrations, e.g., low fluorine ($F_2$) concentrations, in addition to the poor heat exchange, there are also ineffective (reaction) zones with (inert) gas bubbles, which nullifies the advantages of using a coil reactor or a microreactor, and the same is observed in bed tower reactor (gas scrubber system) technology.

However, it was also found by the present invention that, based on the total fluorination gas composition as 100% by volume, increasing the concentration of elemental fluorine ($F_2$) in the fluorination gas to a higher concentration of greater than 20% by volume, e.g., preferably of greater than 25% by volume, more preferably of greater than 30% by volume or 40% by volume, and most preferably of greater than 50% by volume, while on the other hand decreasing the concentration of the inert gas, e.g., of the inert gas nitrogen ($N_2$), to a corresponding lower concentration of less than 80% by volume, e.g., preferably of less than 75% by volume, more preferably of less than 70% by volume or 60% by volume, and most preferably of less than 50% by volume, for an industrial process gradually increasing conversion rates of essentially above about 30 to 45%, e.g. conversion rates of more than 50% by volume, preferably of more than 60% by volume, or more than 70% by volume, or more than 70% by volume, even more preferably of more than 80% by volume, and most preferably of more than 90% by volume, can be achieved.

Without wishing to be bound to a theory, it is estimated that the inert gas used to dilute the reactivity of the strongly oxidant elemental fluorine ($F_2$), which is required for safety reasons when handling and transporting elemental fluorine ($F_2$) as described in the background above (e.g., in Europe mixtures of 95% by volume N2 (inert gas) with only 5% by volume $F_2$-gas, or in Asia, e.g., at least 80% by volume N2 (inert gas) with only up to 20% by volume $F_2$-gas) is jeopardizing the fluorination reaction, despite the fact that the elemental fluorine ($F_2$) contained in such a diluted fluorination gas still is strong oxidant.

Surprisingly, by the present invention it was found, that direct fluorination of compounds with even higher conversion rates than those obtained with the said conventional diluted fluorination gases can be achieved, if the elemental fluorine ($F_2$) is undiluted by inert gas, or elemental fluorine ($F_2$) is diluted by inert gas only to a concentration of greater than 50% by volume elemental fluorine ($F_2$) in the fluorination gas, based on the total fluorination gas composition as 100% by volume.

Therefore, it is particularly preferred by the present invention to provide a fluorination process for the manufacture or preparation of a fluorinated inorganic compound or a fluorinated organic compound, respectively, by direct fluorination using fluorine gas ($F_2$), as it comes directly out of a $F_2$-electrolysis reactor (fluorine cell).

A representative composition of fluorine gas produced by a fluorine cell is 97% $F_2$, up to 3% $CF_4$ (formed from damage of the electrodes), traces of HF, $NO_2$, $OF_2$, $COF_2$, each % by volume and based on the total volume of the fluorine containing gas as 100% by volume.

Purification of the fluorination gas as it is derived from a $F_2$-electrolysis reactor (fluorine cell), if desired, optionally is possible, to remove a part or all by-products and traces formed in the $F_2$-electrolysis reactor (fluorine cell), prior to its use as fluorination gas in the process of the present invention. However, in the process of the present invention such a partial or complete purification is not required, and the fluorination gas can be directly used, as it comes directly out of a $F_2$-electrolysis reactor (fluorine cell).

When employing a fluorination gas derived from a $F_2$-electrolysis reactor (fluorine cell), purified or unpurified, it may, if desired, optionally be diluted to some extent by an inert gas, preferably by nitrogen ($N_2$).

Hence, such a fluorination gas, purified or unpurified, as it is derived from a $F_2$-electrolysis reactor (fluorine cell), if desired, may optionally be diluted by up to about 45% by volume of inert gas, but preferably the fluorination gas is not diluted by inert gas to a concentration of elemental fluorine ($F_2$) in the fluorination gas of less 80% by volume, preferably of less than 85% by volume, more preferably of less than 90% by volume, based on the total fluorination gas composition as 100% by volume.

The difference of the sum of the elemental fluorine ($F_2$) and any inert gas in the fluorination gas to 100% by volume, if any difference, may be constituted by by-products (e.g., $CF_4$) and traces of HF, $NO_2$, $OF_2$, $COF_2$, formed from damage of the electrodes of the $F_2$-electrolysis reactor (fluorine cell). This applies generally to the % by volume values given herein above and herein below, if fluorine gas ($F_2$), as it comes directly out of a $F_2$-electrolysis reactor (fluorine cell) is used as the fluorination gas in the present invention.

Accordingly, in a preferred process of the invention the direct fluorination is carried out with a fluorination gas comprising about 80% by volume to 97±1% of elemental fluorine ($F_2$) and about 0% to 17±1% of inert gas, preferably of nitrogen ($N_2$), based on the total fluorination gas composition as 100% by volume.

In a further preferred process of the invention the direct fluorination is carried out with a fluorination gas comprising about 85% by volume to 97±1% of elemental fluorine ($F_2$) and about 0% to 12±1% of inert gas, preferably of nitrogen ($N_2$), based on the total fluorination gas composition as 100% by volume.

In a furthermore preferred process of the invention the direct fluorination is carried out with a fluorination gas comprising about 87% by volume to 97±1% of elemental fluorine ($F_2$) and about 0% to 10±1% of inert gas, preferably of nitrogen ($N_2$), based on the total fluorination gas composition as 100% by volume.

In another preferred process of the invention the direct fluorination is carried out with a fluorination gas comprising about 90% by volume to 97±1% of elemental fluorine ($F_2$) and about 0% to 7±1% of inert gas, preferably of nitrogen ($N_2$), based on the total fluorination gas composition as 100% by volume.

In still another preferred process of the invention the direct fluorination is carried out with a fluorination gas comprising about 95% by volume to 97±1% of elemental fluorine ($F_2$) and about 0% to 2±1% of inert gas, preferably of nitrogen ($N_2$), based on the total fluorination gas composition as 100% by volume.

It goes without saying that a person skilled in the art understands that within any of the given ranges any intermediate values and intermediate ranges can be selected, too.

Use of Fluorination Gas with High Concentration of Elemental Fluorine:

The invention also relates to a use of a fluorination gas, wherein elemental fluorine ($F_2$) is present in a high concentration of substantially more than, in particular very much more than 15% by volume or in particular than 20% by volume of elemental fluorine ($F_2$), especially of equal to much higher than 25% by volume, i.e., at least 25% by volume, of elemental fluorine ($F_2$), preferably of equal to much higher than 35% by volume or in particular than 45% by volume, for the manufacture of a fluorinated inorganic compound or a fluorinated organic compound, respectively, in a liquid medium comprising or consisting of an inorganic compound or an organic compound, respectively, each as starting compound (wherein the one or more hydrogen atoms that are capable of being substituted by means of a halogenation reaction), with the proviso that the starting compound is not benzene, not benzoic acid, and not a benzoic acid derivative, and the fluorinated compound produced is not a fluorinated benzene, especially not monofluorobenzene.

In general, in one aspect the invention is also directed to the use of a fluorination gas, wherein the elemental fluorine ($F_2$) is present in a high concentration, e.g., a use in a process for the manufacture of a fluorinated inorganic compound or a fluorinated organic compound, respectively, in a liquid medium comprising or consisting of a starting compound having one or more hydrogen atoms that are capable of being substituted by means of a halogenation reaction, according to the invention, with the proviso that the starting compound is not benzene, not benzoic acid, and not a benzoic acid derivative, and the fluorinated compound produced is not a fluorinated benzene, especially not monofluorobenzene, wherein the elemental fluorine ($F_2$) is present in the fluorination gas in a high concentration of at least 25% by volume, preferably of at least 30% by volume, more preferably of at least 35% by volume, even more preferably of at least 45% by volume, each based on the total volume of the fluorination gas as 100% by volume.

Furthermore, in the said use, the elemental fluorine ($F_2$) can be present in the fluorination gas in a high concentration of at least 45% by volume, preferably of at least 50% by volume, more preferably of at least 60% by volume, even more preferably of at least 70% by volume, or of at least 80% by volume, each based on the total volume of the fluorination gas as 100% by volume.

In the said use for the manufacture of a fluorinated compound according to the invention, in an embodiment the elemental fluorine ($F_2$) is present in the fluorination gas in a high concentration of at least 15% by volume, preferably of at least 20% by volume, or of at least 25% by volume, more preferably of at least 30% by volume, even more preferably of at least 40% by volume, each based on the total volume of the fluorination gas as 100% by volume.

Furthermore, in the said use, the elemental fluorine ($F_2$) can be present in the fluorination gas in a high concentration of at least 45% by volume, preferably of at least 50% by volume, more preferably of at least 60% by volume, even more preferably of at least 70% by volume, or of at least 80% by volume, each based on the total volume of the fluorination gas as 100% by volume.

In the said use for the manufacture of a fluorinated compound according to the invention, in an embodiment the elemental fluorine ($F_2$) is present in the fluorination gas in a high concentration within a range of from 15-100% by volume, preferably within a range of from 20-100% by volume, more preferably within a range of from 25-100% by volume, still more preferably within a range of from 30-100% by volume, even more preferably within a range of from 35-100% by volume, an still more preferred within a range of from 45-100% by volume, each based on the total volume of the fluorination gas as 100% by volume.

Furthermore, in the said use, the elemental fluorine ($F_2$) can be present in the fluorination gas in a high concentration within a range of from 45-100% by volume, preferably within a range of from 50-100% by volume, more preferably within a range of from 60-100% by volume, still more preferably within a range of from 70-100% by volume, even more preferably within a range of from 80-100% by volume, each based on the total volume of the fluorination gas as 100% by volume.

The Process of the Invention:

As briefly described in the Summary of the Invention, and defined in the claims and further detailed by the following description and examples herein, the invention is particularly directed to a process for the manufacture of a fluorinated compound by direct fluorination, wherein the process comprises the steps of:

a) provision of a liquid medium comprising or consisting of a (inorganic or organic) starting compound having one or more hydrogen atoms that are capable of being substituted by means of a halogenation reaction;

b) provision of a fluorination gas comprising or consisting of elemental fluorine ($F_2$), wherein the fluorine is present in the fluorination gas in a high concentration of at least substantially more than, in particular very much more than 15% by volume (vol.-%), preferably equal to or more than 20% by volume (vol.-%);

c) provision of a reactor or reactor system, resistant to elemental fluorine ($F_2$) and hydrogen fluoride (HF);

d) passing the fluorination gas of b), in a reactor or reactor system of c), through the liquid medium of a) comprising or consisting of the (inorganic or organic) starting compound, and thereby reacting the (inorganic or organic) starting compound with the elemental fluorine ($F_2$) to substitute in the (inorganic or organic) starting compound at least one of the one or more hydrogen atoms for fluorine, and wherein the reaction is carried out at temperature of from about −30° C. to about +100° C. and a pressure of from about 1 bar absolute bar to about 20 bar absolute bar;

e) withdrawing the fluorinated (inorganic or organic) compound formed in step d) from the reactor or reactor system of c);

f) to obtain a (inorganic or organic) fluorinated compound wherein at least one of the one or more hydrogen atoms of the starting compound is replaced by fluorine atom;

with the proviso that the starting compound is not benzene, not benzoic acid, and not a benzoic acid derivative, and the fluorinated compound produced is not a fluorinated benzene, especially not fluorobenzene.

In the said process for the manufacture of a fluorinated compound according to the invention, in an embodiment the elemental fluorine ($F_2$) is present in the fluorination gas of b) in a high concentration of at least 25% by volume, preferably of at least 30% by volume, more preferably of at least 35% by volume, even more preferably of at least 45% by volume, each based on the total volume of the fluorination gas as 100% by volume.

In the said process for the manufacture of a fluorinated compound according to the invention, in an embodiment the fluorine ($F_2$) is present in the fluorination gas of b) in a high concentration within a range of from 15-100% by volume, preferably within a range of from 20-100% by volume, more preferably within a range of from 25-100% by volume, still more preferably within a range of from 30-100% by volume, even more preferably within a range of from 35-100% by volume, an still more preferred within a range of from 45-100% by volume, each based on the total volume of the fluorination gas as 100% by volume.

In a further embodiment, in the process for the manufacture of a fluorinated compound according to the invention, the starting compound is an inorganic starting compound, preferably an inorganic starting compound selected from the group consisting of ammonia, hydrogen cyanide, hydrazine, tetrafluorohydrazine, difluorodiazine, sulphur hexafluoride ($SF_6$), and iodine pentafluoride ($IF_5$).

In a still further embodiment, in the process for the manufacture of a fluorinated compound according to the invention, the compound is an organic starting compound, but is not benzene, preferably wherein the starting compound is an organic starting compound selected from the group consisting of acetonitrile, monofluoro acetonitrile, difluoro acetonitrile, methane sulfonic acid fluoride, monofluoromethane sulfonic acid fluoride, difluoromethane sulfonic acid fluoride, methane sulfonic acid fluoride, ethylene carbonate, monofluoroethylene carbonate, difluoroethylene carbonate, trifluoroethylene carbonate, formaldehyde (H2C=O), difluorophosgene ($F_2C=O$), 2,2,2-trifluoroethyl methyl ether, acetic acid ethyl ether, monofluoroacetic acid ethyl ether, difluoroacetic acid ethyl ether, methyl acrylate, a malonic acid diester starting compound, preferably malonic acid dimethyl ester, a 1,3-dicarbonyl methylene starting compound, a C6-aromatic compound, but not benzene, a deactivated benzene derivative, a C10-aromatic compound, a deactivated C10-aromatic compound, a 5-membered heterocyclic compound, a 6-membered heterocylic compound, a 5-membered heteroaromatic compound, a 6-membered heteroaromatic compound, preferably pyridine, uracil, and cytosine.

Batch Process:

The invention also may pertain to a process for the manufacture of a fluorinated compound, wherein the process is a batchwise process, preferably wherein the batchwise process is carried out in a column reactor. Although, in the following reactor setting the process is described as a batch process, as preferred, for example, in case of high product concentrations, optionally the process can be performed in the said reactor setting also as a continuous process. In case of a continuous process in the said reactor setting, then, it goes without saying, the additional inlet(s) and outlet(s) are foreseen, for feeding the starting compound and withdrawing the product compound, respectively.

If the invention pertains to a batchwise process, preferably wherein the batchwise process is carried out in a column reactor, the process for the manufacture of a fluorinated compound according, most preferably the reaction is carried out in a (closed) column reactor (system), wherein the liquid medium of a) comprising or consisting of the starting compound is circulated in a loop, while the fluorination gas of b) comprising or consisting of elemental fluorine (F2) in a high concentration is fed into the column reactor of c) and in step d) is passed through the liquid medium to react with the starting compound; preferably wherein the loop is operated with a circulation velocity of from 1,500 l/h to 5,000 l/h, more preferably of from 3,500 l/h to 4,500 l/h.

If the invention pertains to a batchwise process, the process for the manufacture of a fluorinated compound according to the invention can be carried out such that the liquid medium of a) comprising or consisting of the starting compound is circulated in the column reactor in a turbulent stream or in laminar stream, preferably in a turbulent stream.

In general, the fluorination gas containing the elemental fluorine ($F_2$) is fed into the loop in accordance with the required stoichiometry for the targeted fluorinated product and fluorination degree, and adapted to the reaction rate.

For example, the said process for the manufacture of a fluorinated compound according to the invention, may be performed, e.g., batchwise, wherein the column reactor is equipped with at least one of the following: at least one cooler (system), at least one liquid reservoir for the liquid medium of a) comprising or consisting of a starting compound, a pump (for pumping/circulating the liquid medium), one or more (nozzle) jets, preferably placed at the top of the column reactor, for spraying the circulating medium into the column reactor, one or more feeding inlets for introducing the fluorination gas of b) comprising or consisting of elemental fluorine ($F_2$) in a high concentration, optionally one or more sieves, preferably two sieves, preferably the one or more sieves placed at the bottom of the column reactor, at least one gas outlet equipped with a pressure valve.

Accordingly, the process for the manufacture of a fluorinated compound according to the invention, can be performed in column reactor which is equipped with at least one of the following:

(i) at least one cooler (system), at least one liquid reservoir, with inlet and outlet for, and containing the liquid medium of a) comprising or consisting of an inorganic compound or organic compound as the starting compound;

(ii) a pump for pumping and circulating the liquid medium of a);

(iii) one or more (nozzle) jets, preferably wherein the one or more (nozzle) jets are placed at the top of the column reactor, for spraying the circulating medium of a) into the column reactor;

(iv) one or more feeding inlets for introducing the fluorination gas of b) comprising or consisting of elemental fluorine ($F_2$) in a high concentration into the column reactor;

(v) optionally one or more sieves, preferably two sieves, preferably the one or more sieves placed at the bottom of the column reactor;

(vi) and at least one gas outlet equipped with a pressure valve, and at least one outlet for withdrawing the fluorinated inorganic compound or organic compound in step e).

In one embodiment, the process for the manufacture of a fluorinated compound according to the invention, can be performed in a column reactor is a packed bed tower reactor, preferably a packed bed tower reactor which is packed with fillers resistant to elemental fluorine ($F_2$) and hydrogen fluoride (HF), e.g. with Raschig fillers and/or metal fillers, more preferably wherein the packed bed tower reactor is a gas scrubber system (tower) which is packed with fillers resistant to elemental fluorine ($F_2$) and hydrogen fluoride (HF), e.g. Raschig fillers and/or metal fillers.

In a further embodiment, the process for the manufacture of a fluorinated compound according to the invention, the reaction is carried out with a counter-current flow of the circulating liquid medium of a) comprising or consisting of the starting compound and of the fluorination gas of b) fed into the column reactor and which fluorination gas of b) is comprising or consisting of elemental fluorine ($F_2$) in a high concentration.

The pressure valve functions to keep the pressure, as required in the reaction, and to release any effluent gas, e.g. inert carrier gas contained in the fluorination gas, if applicable together with any hydrogen fluoride (HF) released for the reaction.

The said process for the manufacture of a fluorinated compound according to the invention, may be performed, e.g., batchwise, such that in the said process for the manufacture of a fluorinated compound the column reactor is a packed bed tower reactor, preferably a packed bed tower reactor which is packed with metal fillers.

The packed tower according to FIG. 1 can have a diameter of 100 or 200 mm (depending on the circulating flow rate and scale) made out of high grade stainless steel (1.4571) and a length of 3 meters for the 100 mm and a length of 6 meters for the 200 mm diameter tower (latter if higher capacities are needed). The tower made out of Hastelloy is filled either with E-TFE or metal fillings each of 10 mm diameter as available from Raschig (http://www.raschig.de/Fllkrper). The type of fillings is quite flexible, Raschigs Pall-Rings made out of Hastelloy were used in the trials disclosed hereunder, also E-TFE-fillings showed same performance, both not causing too much pressure reduction (pressure loss) while feeding $F_2$-gas in counter-current manner.

In the process for the manufacture of a fluorinated compound according to any of the embodiments of the invention, the reaction may be carried out with a counter-current flow of circulating liquid medium of a) comprising or consisting of the starting compound and the fluorination gas of b) fed into the column reactor and comprising or consisting of elemental fluorine ($F_2$) in a high concentration.

Microreactor Process:

The invention also may pertain to a process for the manufacture of a fluorinated compound according to any of the preceding claims, wherein the process is a continuous process, preferably wherein the continuous process is carried out in a microreactor. See FIG. 2.

In general, the fluorination gas containing the elemental fluorine (F2) is fed into the microreactor in accordance with the required stoichiometry (sometimes with a slight excess) for the targeted fluorinated product and fluorination degree, and adapted to the reaction rate.

The invention may employ more than a single microreactor, i.e., the invention may employ two, three, four, five or more microreactors, for either extending the capacity or residence time, for example, to up to ten microreactors in parallel or four microreactors in series. If more than a single microreactor is employed, then the plurality of microreactors can be arranged either sequentially or in parallel, and if three or more microreactors are employed, these may be arranged sequentially, in parallel or both.

The invention is also very advantageous, in one embodiment wherein the direct fluorination of the invention optionally is performed in a continuous flow reactor system, or preferably in a microreactor system.

In an preferred embodiment the invention relates to a process for the manufacture of a fluorinated compound according to the invention, wherein the reaction is carried out in at least one step as a continuous processes, wherein the continuous process is performed in at least one continuous flow reactor with upper lateral dimensions of about ≤5 mm, or of about ≤4 mm, preferably in at least one microreactor;

more preferably wherein of the said steps at least (b2) the step of a fluorination reaction is a continuous process in at least one microreactor under one or more of the following conditions:
flow rate: of from about 10 ml/h up to about 400 l/h;
temperature: of from about 30° C. up to about 150° C.;
pressure: of from about 4 bar up to about 50 bar;
residence time: of from about 1 second, preferably from about 1 minute, up to about 60 minutes.

In another preferred embodiment the invention relates to such a process of preparing a compound according to the invention, wherein at least one of the said continuous flow reactors, preferably at least one of the microreactors, independently is a SiC-continuous flow reactor, preferably independently is a SiC-microreactor.

The Continuous Flow Reactors and Microreactors:

In addition to the above, according to one aspect of the invention, also a plant engineering invention is provided, as used in the process invention and described herein, pertaining to the optional, and in some embodiments of the process invention, the process even preferred implementation in microreactors.

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤5 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. <1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly, just a larger volume reactor can be used and/or even several microreactors can be placed in series, optionally just having some cylinders in between for increasing residence time if necessary for completion of reaction steps. In this later case, cyclones after each microreactor help to let formed HCl to escape and to positively influence the reaction performance. Production rates can vary from milliliters per minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

In the use and processes according to the invention in a preferred embodiment the invention is using a microreactor. But it is to be noted in a more general embodiment of the invention, apart from the said preferred embodiment of the invention that is using a microreactor, any other, e.g. preferentially pipe-like, continuous flow reactor with upper lateral dimensions of up to about 1 cm, and as defined herein, can be employed. Thus, such a continuous flow reactor preferably with upper lateral dimensions of up to about ≤5 mm, or of about ≤4 mm, refers to a preferred embodiment of the invention, e.g. preferably to amicroreactor. Continuously operated series of STRs is another option, but less preferred than using a microreactor.

In the before said embodiments of the invention, the minimal lateral dimensions of the, e.g. preferentially pipe-like, continuous flow reactor can be about >5 mm; but is usually not exceeding about 1 cm. Thus, the lateral dimensions of the, e.g. preferentially pipe-like, continuous flow reactor can be in the range of from about >5 mm up to about 1 cm, and can be of any value therein between. For example, the lateral dimensions of the, e.g. preferentially pipe-like, continuous flow reactor can be about 5.1 mm, about 5.5 mm, about 6 mm, about 6.5 mm, about 7 mm, about 7.5 mm, about 8 mm, about 8.5 mm, about 9 mm, about 9.5 mm, and about 10 mm, or can be can be of any value intermediate between the said values.

In the before said embodiments of the invention using a microreactor preferentially the minimal lateral dimensions of the microreactor can be at least about 0.25 mm, and preferably at least about 0.5 mm; but the maximum lateral dimensions of the microreactor does not exceed about ≤5 mm. Thus, the lateral dimensions of the, e.g. preferential microreactor can be in the range of from about 0.25 mm up to about ≤5 mm, and preferably from about 0.5 mm up to about ≤5 mm, and can be of any value therein between. For example, the lateral dimensions of the preferential microreactor can be about 0.25 mm, about 0.3 mm, about 0.35 mm, about 0.4 mm, about 0.45 mm, and about 5 mm, or can be can be of any value intermediate between the said values.

As stated here before in the embodiments of the invention in its broadest meaning is employing, preferentially pipe-like, continuous flow reactor with upper lateral dimensions of up to about 1 cm. Such continuous flow reactor, for example is a plug flow reactor (PFR).

The plug flow reactor (PFR), sometimes called continuous tubular reactor, CTR, or piston flow reactors, is a reactor used to perform and describe chemical reactions in continuous, flowing systems of cylindrical geometry. The PFR reactor model is used to predict the behaviour of chemical reactors of such design, so that key reactor variables, such as the dimensions of the reactor, can be estimated.

Fluid going through a PFR may be modelled as flowing through the reactor as a series of infinitely thin coherent "plugs", each with a uniform composition, traveling in the axial direction of the reactor, with each plug having a different composition from the ones before and after it. The key assumption is that as a plug flows through a PFR, the fluid is perfectly mixed in the radial direction (i.e. in the lateral direction) but not in the axial direction (forwards or backwards).

Accordingly, the terms used herein to define the reactor type used in the context of the invention such like "continuous flow reactor", "plug flow reactor", "tubular reactor", "continuous flow reactor system", "plug flow reactor system", "tubular reactor system", "continuous flow system", "plug flow system", "tubular system" are synonymous to each other and interchangeably by each other.

The reactor or system may be arranged as a multitude of tubes, which may be, for example, linear, looped, meandering, circled, coiled, or combinations thereof. If coiled, for example, then the reactor or system is also called "coiled reactor" or "coiled system".

In the radial direction, i.e. in the lateral direction, such reactor or system may have an inner diameter or an inner cross-section dimension (i.e. radial dimension or lateral dimension, respectively) of up to about 1 cm. Thus, in an embodiment the lateral dimension of the reactor or system may be in the range of from about 0.25 mm up to about 1 cm, preferably of from about 0.5 mm up to about 1 cm, and more preferably of from about 1 mm up to about 1 cm.

In further embodiments the lateral dimension of the reactor or system may be in the range of from about >5 mm to about 1 cm, or of from about 5.1 mm to about 1 cm.

If the lateral dimension at maximum of up to about ≤5 mm, or of up to about ≤4 mm, then the reactor is called "microreactor". Thus, in still further microreactor embodiments the lateral dimension of the reactor or system may be in the range of from about 0.25 mm up to about ≤5 mm, preferably of from about 0.5 mm up to about ≤5 mm, and more preferably of from about 1 mm up to about ≤5 mm; or the lateral dimension of the reactor or system may be in the range of from about 0.25 mm up to about ≤4 mm, preferably of from about 0.5 mm up to about ≤4 mm, and more preferably of from about 1 mm up to about ≤4 mm.

In case reactants are solid inert solvents may be used. Thus, if raw materials shall be used, then the said solid raw materials are dissolved in an inert solvent. A suitable solvent is e.g. acetonitrile, or fully or partially fluorinated alkanes like Pentafluorobutane (365mfc), linear or cyclic partially or fully fluorinated ethers like $CF_3$—$CH_2$—$OCHF_2$ (E245) or Octafluorotetrahydrofuran. Often, if available or after a first synthesis, the product as such can also serve as inert solvent.

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the plug flow reactor and/or a tubular flow reactor, employed in this embodiment of the invention is configured with the construction materials as defined herein for the microreactors. For example, such construction materials are silicon carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

In addition to the preferred embodiments of the present invention using a microreactor according to the invention, in addition or alternatively to using a microreactor, it is also possible to employ a plug flow reactor or a tubular flow reactor, respectively.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, respectively, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic continuous flow reactor, more preferably a SiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

For example, in the embodiments of the invention the objects are achieved by a method in which at least one reaction step takes place in a microreactor. Particularly, in preferred embodiments of the invention the objects are achieved by a method in which at least one reaction step takes place in a microreactor that is comprising or is made of SiC ("SiC-microreactor"), or in a microreactor that is comprising or is made of an alloy, e.g. such as Hastelloy C, as it is each defined herein after in more detail.

Thus, without being limited to, for example, in an embodiment of the invention the microreactor suitable for, preferably for industrial, production an "SiC-microreactor" that is comprising or is made of SiC (silicon carbide; e.g. SiC as offered by Dow Corning as Type G1 SiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld. Such microreactors are particularly suitable for the, preferably industrial, production of fluorinated products according to the invention.

In order to meet both the mechanical and chemical demands placed on production scale flow reactors, Plantrix modules are fabricated from 3M™SiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 B1 and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10\text{-}6K^{-1}$).

Designed for flow rates ranging from 0.2 to 20 ml/min and pressures up to 25 bar, Protrix® allows the user to develop continuous flow processes at the lab-scale, later transitioning to Plantrix® MR555 (×340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarised as follows: possible reaction types are, e.g. A+B→P1+Q (or C)→P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300×250; number of modules/frame is one (minimum) up to four (max.). More technical information on the ChemtrixProtrix® reactor can be found in the brochure "CHEMTRIX—Scalable Flow Chemistry—Technical Information Protrix®, published by Chemtrix BV in 2017, which technical information is incorporated herein by reference in its entirety.

The Dow Corning as Type G1 SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1 SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type G1 SiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively. The reactor configuration of Dow Corning as Type G1 SiC microreactor is characterized as multipurpose and configuration can be customized. Injection points may be added anywhere on the said reactor.

Hastelloy® C is an alloy represented by the formula NiCr21Mo14W, alternatively also known as "alloy 22" or "Hastelloy® C-22. The said alloy is well known as a highly corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0,35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%. Normally, no traceable amounts of any of the following elements are found in the alloy compositions indicated above: Nb (niobium), Ti (titanium), Al (aluminum), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

In another embodiments of the invention, without being limited to, for example, the microreactor suitable for the said production, preferably for the said industrial production, is an SiC-microreactor that is comprising or is made only of SiC as the construction material (silicon carbide; e.g. SiC as offered by Dow Corning as Type G1 SiC or by ChemtrixMR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of the fluorinated products according to the invention. If more than one microreactor, preferably more than one SiC-microreactors, are used in the production, preferably in the industrial production, of the fluorinated products according to the invention, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable. Sometimes, if gaskets of a microreactor are made out of other material than HDPTFE, leakage might occur quite soon after short time of operation because of some swelling, so HDPTFE gaskets secure long operating time of microreactor and involved other equipment parts like settler and distillation columns.

For example, an industrial flow reactor ("IFR", e.g. Plantrix® MR555) comprises of SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MRX") that affords access to A+B→P type reactions. Increasing the number of modules leads to increased reaction times and/or system productivity. The addition of a quench Q/C module extends reaction types to A+B→P1+Q (or C)→P and a blanking plate gives two temperature zones. Herein the terms "A", "B" and "C" represent educts, "P" and "P1" products, and "Q" quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MRH" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)<70° C.; reagent feeds of 1 to 3; maximum operating pressure (service fluid) of about 5 bar at a temperature of about 200° C.; maximum operating pressure (process fluid) of about 25 bar at a temperature of about ≤200° C.

Use of a Fluorination Gas in Direct Fluorination:

In a particular embodiment, the present invention, in generally is directed also to a use of a fluorination gas, wherein elemental fluorine ($F_2$) is present in a high concentration of substantially more than, in particular very much more than 15% by volume or in particular than 20% by volume of elemental fluorine ($F_2$), especially of equal to much higher than 25% by volume, i.e., at least 25% by volume, of elemental fluorine ($F_2$), preferably of equal to much higher than 35% by volume or in particular than 45% by volume, for the manufacture of a fluorinated compound in a liquid medium comprising or consisting of a starting compound having one or more hydrogen atoms that are capable of being substituted by means of a halogenation reaction; preferably wherein the fluorine ($F_2$) is present in the fluorine containing gas in a high concentration in a range of from 15-100% by volume, preferably within a range of from 20-100% by volume, more preferably within a range of from 25-100% by volume, still more preferably within a range of from 30-100% by volume, even more preferably within a range of from 35-100% by volume, an still more preferred within a range of from 45-100% by volume, each based on the total volume of the fluorination gas as 100% by volume; with the proviso that the starting compound is not benzene, not benzoic acid, and not a benzoic acid derivative, and the fluorinated compound produced is not a fluorinated benzene, especially not monofluorobenzene.

The following examples are intended to further illustrate the invention without limiting its scope.

EXAMPLES

Following compounds or intermediates are prepared according to this invention:

Example 1

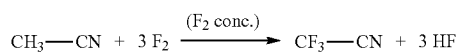

Reference to state of the art: U.S. Pat. No. 2,745,867, preparation over trichloroacetonitrile followed by fluorination with HF with CrO3 catalyst in gas phase to trifluoroacetonitrile
  a) By electrochemistry: in U.S. Pat. No. 3,017,336 in a special CN-containing electrolyte, carbon atom comes from anode material→not industrial feasible.
  b) Out of trifluoroacetic acid amide and $P_2O_5$ in CN 10274619.

Process of the Invention:

In a Batch fluorination counter-current apparatus having a pressure valve at the top which is set to 20 bar and with a total volume of 10 l (see drawing 1), 4.0 kg (97.4 mol, 5.1 l) of absolute acetonitrile were filled and the pump was started. The for the cooler a water cooling with a water temperature of 8° C. was used. When the temperature of the acetonitrile reached 15° C., the conc. $F_2$ valve was opened with a dosage of 20 mol $F_2$ gas/h. For this trial, the $F_2$-gas had a concentration of 97%/h. Some purge gas leaves the apparatus together with slightly overdosed $F_2$. In total, 321.4 mol (6.11 kg) $F_2$ gas was fed over 5 h over a mass flow controller from Bronkhorst into the looping reaction mixture. Reaction samples were taken very carefully with a stainless steel cylinder (a sealed sampling system) after each hour. For analysis, the samples were hydrolyzed with same volume of water, the organic phase dried over $Na_2SO_4$ and injected into a Hewlett Packard Gas chromatography system. The sample taken after 5 h contained 96% $CF_3CN$.

(Batch) Work Up Procedure a)

The reaction mixture was fed slowly into water into a PTFE coated settler (tank with 20 bar), after decanting the water, the organic phase was looped over a sieve with $Na_2SO_4$ for drying purpose and subjected to a fine distillation at 15 bar pressure in a stainless steel column cooled with −20° C. at the top cooler, all made out of 1.4771 high grade stainless steel. Over the top, a pre-fraction of CF$_3$CN together with HF left first, afterwards 7.9 kg of pure CF$_3$CN (85% yield, 99.5% purity) could be obtained.

Continuous Work Up Procedure Using 2 Stainless Steel Columns b)

In said fluorination apparatus, a side stream taken after the counter-current pump over a valve (valve bought from company Best) was continuously taken out the counter-current stream (stream back to the nozzles only little bit open) and is fed continuously into the middle part of a stainless steel distillation column made out of 1.4571 steel which had a total volume of 2 liters. The pressure in the column is kept at 20 bar and the top condenser of the column is cooled with a cooling liquid down to −20° C. (reflux of liquid CF$_3$CN). As there are only small amounts of CH$_3$CN present after reaction, the bottom of the column is not emptied at all but at the top boiler continuously CF$_3$CN is removed into a stainless steel bottle staying in a cooling bath of CO$_2$. The isolated yield after distillation was 89%.

Figure 3:
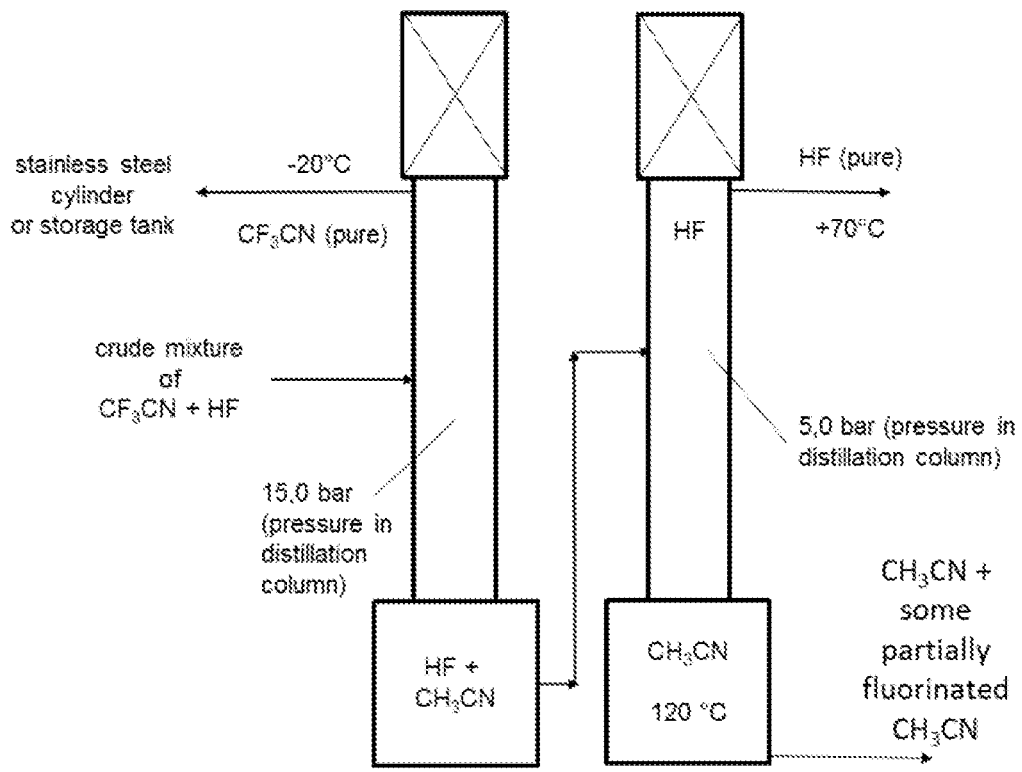
FIG. 3 shows continuous distillation of CF3CN out of synthesis with F2.

Continuous distillation of CF$_3$CN out of synthesis with F$_2$. See FIG. 3.

The fluorination product can be used as raw material to prepare a conducting salt for lithium batteries.

Example 2

The fluorination of CH$_3$CN was repeated continuously in a microreactor system using in lab a 27 ml SiCmicroreactor from Chemtrix. The CH$_3$CN and F$_2$ feed was set to a molar ratio of 1:3.1 and the reactor was kept at 5° C. The liquid feed was 234 g (5.7 mol, 300 ml) CH$_3$CN per hour. The F$_2$-gas stream, which come directly from a fluorine electrolysis cell (controlled with a Bronkhorst mass flow meter), was fed together with the CH$_3$CN in a split and re-combine system before it entered into the microreactor channels. The achieved yield after continuous 2 column distillation like described in example 1 gave a CF$_3$CN yield of 96%.

Example 3

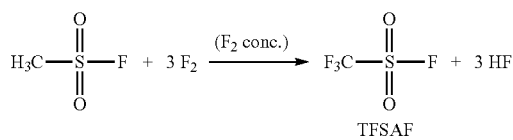

TFSAF

Methane sulfonic acid fluoride was fluorinated in batch at 10° C. according to Example 1. The yield was 78% after a continuous fine distillation.

The fluorination product trifluoromethane sulfonyl fluoride (TFSAF) gives triflic acid after hydrolysis or can be used as raw material to prepare LiTFSI (Li-salt of 1,1,1-trifluoro-N-[(trifluoromethyl)sulfonyl]-methanesulfonamide).

Example 4

The fluorination of methane sulfonic acid fluoride was done in a 27 ml SiCmicroreactor (see Example 2). The achieved yield was 98%.

Example 5

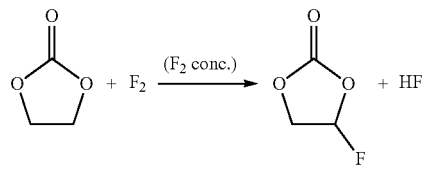

The fluorination was done in a microreactor system at 10° C. (see Example 2). The achieved yield was 94%.

Example 6

Preparation of F—CN (Analogous to Cl—CN):

In the prior art Cl—CN is described by synthesis with Cl2 to give Cl—CN; see for example, WO 2014/065422 and Maugin, Ch.; Simon, L.-J., in Annali di ChimicaApplicata (1921)15, 18-41). F—CN is only described in the prior art by synthesis out of Cl—CN by Seel, Fritz; Ballreich, Kurt in ChemischeBerichte (1959)92, 344-6 or 2,4,6-Trifluoro-s-triazine by Wu, Y.-Q. in Science of Synthesis (2005)18, 17-63).

Process according to the invention:

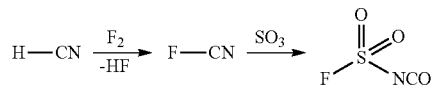

Advantage here is a very high purity of the bis-fluorosulfonyl imide as the fluorine atom is in the molecule before formation of the amide. Fluorination of any chlorosulfonyl-bis-amide also gives the bis-fluorosulfonyl imide but all fluorinating agents and fluorination methods leave impurities which cannot or only be removed with much efforts. Very high purities are needed for usage as conducting salt in battery electrolytes.

The fluorination product can be used as raw material to prepare a conducting salt for lithium batteries.

Example 7

Synthesis of NF3 NF3 is prepared out of F$_2$ and N-Plasma like in U.S. Pat. No. 3,961,024 without catalyst or metal fluoride catalyst or like in U.S. Pat. No. 3,304,248, or out of NH$_3$ and F$_2$ under Cu catalysis like in U.S. Pat. No. 3,214,237 or even out of C—F compounds like in U.S. Pat. No. 3,043,662 or in newer applications out of NH$_4$xHF and F$_2$ gas like in U.S. Pat. No. 4,091,081, JP 55008926 and JP 03236487. All known methods are either very difficult to perform and even dangerous (strongly oxidizing materials to handle), have low yield and or high energy consumption like in DE 3722163, JP 04131391 and CN 103896223 in the synthesis by electrolysis or in special apparatus like in JP 02255512. Very often, due to safety, additional gases like CF$_4$ and others are either added like in JP 02255513. In electrolysis, most always much CF$_4$ is formed in situ out of carbon electrode material. This CF$_4$ must be removed for commercial applications. This invention discloses the safe synthesis of NF$_3$ out of NH$_3$ and/or H2N—NH$_2$ using concentrated F$_2$ gas in micoreactors and the preparation of a technical grade material. Besides safety this procedure has the advantage that NO CF$_4$ is formed which finally leads to a less challenging purification. Semiconductor grade material can be made e.g. according to WO 2017138366, KR 2017023281, CN 106276828, CN 103896224 and many other procedures.

Inventive: Continuous synthesis of $NF_3$ in microreactor.

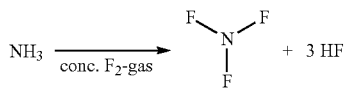

In the microreactor apparatus as given in FIG. 2 (see also Example 2), 3.01 mol/h high concentrated $F_2$ gas from $F_2$ production electrolysis (over a Bronkhorst flow meter) was fed together with 1 mol/h $NH_3$ from a $NH_3$ tank into a 27 ml SiCmicroreactor from Chemtrix at 60° C. A second microreactor was added in series just to extend residence time and to have a better temperature and pressure control for the reaction. The leaving material was collected in a stainless steel cylinder cooled by liquid nitrogen.

Example 8

Conversion of Tetrafluorohydrazine $N_2F_4$ to $NF_3$ $N_2F_4$ can be co-produced respectively is formed as side product by existing electrolysis plants to make $NF_3$ out of $NH_4F \times HF$ by electrolysis. Also the conversion of this $N_2F_4$ containing already larger amounts of $NF_3$ is included into this invention as a purification step using microreactor technology which is easier than e.g. absorption methods as described in EP 366078 or JP 03208806.

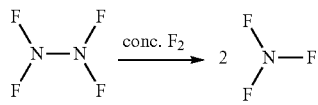

The amount of $F_2$ fed into the microreactor at parameters like in Example 7 (see also FIG. 2) is 5% above the $N_2F_4$ content. In an typical example, 90% $NF_3$/10% $N_2F_4$ containing gas was fed into a microreactor together with $F_2$. The leaving material contained no $N_2F_4$ anymore.

Example 9

Converson of Difluorodiazine $N_2F_2$ to $NF_3$.

$N_2F_2$ also can be a side product in $NF_3$ preparation processes and can be purified by using microreactor technology.

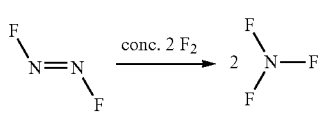

5% $N_2F_2$ containing $NF_3$ gas was treated with conc. $F_2$ in a microreactor (see also FIG. 2, and Example 2). No $N_2F_2$ could be detected any more after the reactor.

Example 10

Purification of $NF_3$ out of example 7 (–9) to a technical grade product.

In 2 stainless steel columns $NF_3$ and HF as achieved in example 7 were fed continuously into a 2 stainless steel column apparatus having 2 l volume each in the bottom. For a stable pressure and a continuous feed into the columns a membrane compressor either directly added after the microreactor or connected to the stainless steel cylinder with previously collected crude material was used. At 50 bar pressure and a $NF_3$ reflux at –30° C., a 99.9 technical grade $NF_3$ was continuously collected. HF is isolated at the top of a second column as illustrated below. This is a general method to purify $NF_3$ also product produced by electrolysis from which the tars in the bottom of the second column comes from.

Figure 4:
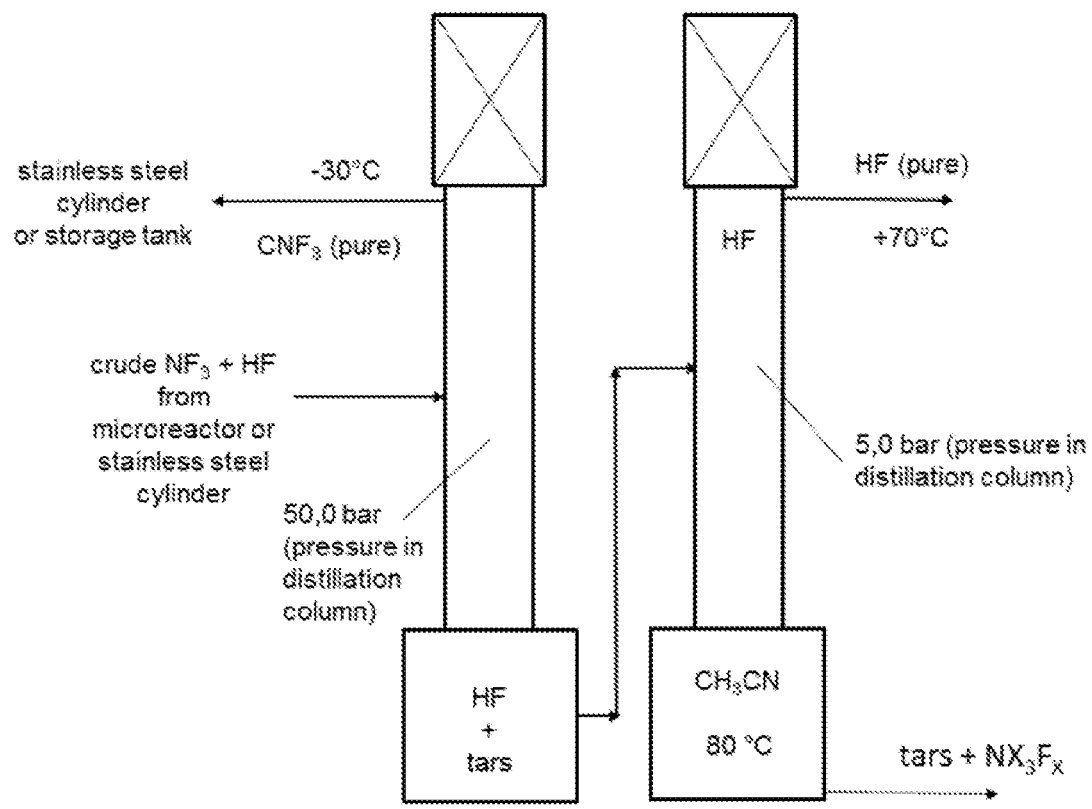
FIG. 4 shows continuous distillation of NF3 crude material out of synthesis with high conc. F2.

Continuous distillation of $NF_3$ crude material out of synthesis with high conc. $F_2$. See FIG. 4.

Example 11

Synthesis of Monofluoromalonate.
Direct fluorination was described already out of the Na-salts and by direct fluorination or even out of diazomalonate, both known procedures, however, are more sophisticated than inventive method hereunder.

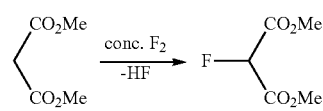

The fluorination of methylmalonate was done continuously in a microreactor system using in lab a 27 ml SiCmicroreactor from Chemtrix (see also FIG. 2, and Example 2). The malonate/$F_2$ feed was set to a molar ratio of 1 to 1.01 and the reactor was kept at 5° C. The liquid feed was 200 g (1.51 mol) Malonate per hour. The $F_2$-gas stream, which comes directly from a fluorine electrolysis cell (controlled with a Bronkhorst mass flow meter), was fed together with the malonate into a split and re-combine system before it entered into the microreactor channels but a trial without that premixer showed almost same results. Samples for reaction control were taken and just slowly hydrolyzed into ice water to get rid of HF, the organic phase directly injected into GC (gas choromatography) without further purification and without drying. All material leaving the microreactor were collected in a reservoir with a small condenser, collected material was kept at 0° C. The monofluoromalonate was obtained in pure form (90% purity) and a yield of 94% after fine distillation (bp: 111° C.) over a stainless steel column (10 cm length, filled with 10 mm Raschig Rings of PE) at atmospheric pressure.

Example 12

Continuous Purification of FluoromalonateRaw Material.
In two stainless steel columns in series (see also FIG. 1, and Example 1), the raw material out of trial 11 was fed continuously into the first column separating the HF at 21° C. at the top of the first column. The bottom HF free material containing some impurities and the fluorolalonate was fed into the second column yielding the pure fluoromalonate at the top of the second column at 11° C. 94% of the mass fed into this distillation system could be re-collected.

Example 13

Reaction of 1,3-Dinitrobenzene with Highly Concentrated $F_2$.

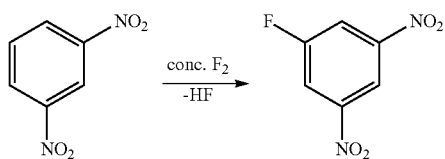 [SMILES: O=[N+]([O-])c1cccc([N+](=O)[O-])c1 ; "-HF" ; O=[N+]([O-])c1cc(F)cc([N+](=O)[O-])c1]

In the microreactor apparatus system as given herein (see also FIG. 2) with two 27 ml microreactors from Chemtrix, 104.5 g/h (2.75 mol/h) high concentrated $F_2$ gas from $F_2$ production electrolysis (over a Bronkhorst flow meter) was fed together with 470.7 g/h (2.8 mol/h) 1,3-dinitro-benzene in $CH_3CN$ from a storage reservoir (tank), both microreactors were heated to 70° C., the pressure was adjusted at 2 bar absolute by a pressure valve after the second microreactor (the second microreactor in series is just to extend residence time and to have a better temperature and pressure control for the reaction). The leaving material after the pressure valve was collected in a cooled stainless steel cylinder followed by a scrubber where the material coming from the microreactors enters the cylinder over a deep pipe. Workup was done by feeding the product mixture into ice water to remove the HF. The organic phase was analyzed by GC-MS and showed no starting material. A fine distillation of the organic phase (after removing the solvent $CH_3CN$ at a rotavapor) at 0.01 mbar and a condenser temperature of 30° C. delivered 1-fluoro-2,4-dinitro-benzene at 149° C. transition temperature. At 20° C., the distilled material became crystalline. The isolated yield was about 89% of theory (about 455 g) in one hour of reaction time.

Example 14

Reaction of 3-Nitro-benzonitrile with Highly Concentrated $F_2$.

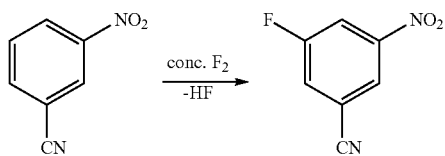 [SMILES: N#Cc1cccc([N+](=O)[O-])c1 ; "-HF" ; N#Cc1cc(F)cc([N+](=O)[O-])c1]

In the microreactor apparatus system as given herein (see also FIG. 2) with two 27 ml microreactors from Chemtrix, 100.0 g/h (2.63 mol/h) highly concentrated $F_2$ gas from $F_2$ production electrolysis (over a Bronkhorst flow meter) was fed together with 399.9 g/h (2.7 mol/h) 3-nitro-benzonitrile in $CH_3CN$ from a storage reservoir (tank), both microreactors were heated to 90° C., the pressure was adjusted at 2 bar absolute by a pressure valve after the second microreactor (the second microreactor in series is just to extend residence time and to have a better temperature and pressure control for the reaction). The leaving material after the pressure valve was collected in a cooled stainless steel cylinder followed by a scrubber where the material coming from the microreactors enters the cylinder over a deep pipe. Workup was done by feeding the product mixture into ice water to remove the HF. The organic phase was analyzed by GC-MS and showed only traces of starting material. The solvent was removed at a rotavapor and the residue distilled at 0.01 mbar at a transition temperature of 155° C., giving about 345 g (about 79% of theory) of 3-fluoro-5-nitro-benzonitrile, in one hour of reaction time.

What is claimed is:

1. A process for the manufacture of a fluorinated compound by direct fluorination, wherein the process comprises the steps of:
   a) provision of a liquid medium comprising a starting compound having one or more hydrogen atoms that are capable of being substituted by means of a halogenation reaction;
   b) provision of a fluorination gas comprising elemental fluorine ($F_2$), wherein the fluorine is present in the fluorination gas in a concentration of equal to or more than 20% by volume based on the total volume of the fluorination gas as 100% by volume;
   c) provision of a reactor or reactor system, resistant to elemental fluorine ($F_2$) and hydrogen fluoride (HF);
   d) passing the fluorination gas of b) through the liquid medium of a) in a reactor or reactor system of c), and thereby reacting the starting compound with the elemental fluorine ($F_2$) to substitute in the starting compound at least one of the one or more hydrogen atoms for fluorine, and wherein the reaction is carried out at temperature of from about −30° C. to about +100° C. and a pressure of from about 1 bar absolute bar to about 20 bar absolute;
   e) withdrawing the fluorinated compound formed in step d) from the reactor or reactor system of c);
   f) to obtain a fluorinated compound wherein at least one of the one or more hydrogen atoms of the starting compound is replaced by a fluorine atom;
   wherein the reaction is carried out in a column reactor, wherein the liquid medium of a) comprising the starting compound is circulated in a loop, while the fluorination gas of b) comprising elemental fluorine ($F_2$) is fed into the column reactor of c) and in step d) is passed through the liquid medium to react with the starting compound wherein the loop is operated with a circulation velocity of from 1,500l/h to 5,000 l/h;
   wherein the column reactor is vertical and equipped with the following:
      (i) at least one cooler and at least one liquid reservoir both having an inlet and an outlet for the liquid medium of a);
      (ii) a pump for pumping and circulating the liquid medium of a);
      (iii) one or more jets, placed at the top of the column reactor, for spraying the circulating medium of a) into the column reactor;
      (iv) one or more feeding inlets for introducing the fluorination gas of b) comprising elemental fluorine ($F_2$) into the column reactor;
      (v) one or more sieves placed at the bottom of the column reactor; and
      (vi) at least one gas outlet equipped with a pressure valve, and at least one outlet for withdrawing the fluorinated compound in step e);
   with the proviso that the starting compound is not benzene and not benzoic acid.

2. The process for the manufacture of a fluorinated compound according to claim 1, wherein the elemental fluorine ($F_2$) is present in the fluorination gas of b) in a concentration of at least 45% by volume.

3. The process for the manufacture of a fluorinated compound according to claim 1, wherein the starting compound is an organic starting compound selected from the group consisting of acetonitrile, monofluoro acetonitrile, difluoroacetonitrile, methane sulfonic acid fluoride, monofluoromethane sulfonic acid fluoride, difluoromethane sulfonic acid fluoride, ethylene carbonate, monofluoroethylene carbonate, difluoroethylene carbonate, trifluoroethylene carbonate, formaldehyde ($H_2C=O$) 2,2,2-trifluoroethyl methyl ether, methyl acrylate, a malonic acid diester starting compound, a 1,3-dicarbonyl methylene starting compound, a C6-aromatic compound, a deactivated benzene derivative, a C10-aromatic compound, a deactivated C10-aromatic compound, a 5-membered heterocyclic compound, a 6-membered heterocylic compound, a 5-membered heteroaromatic compound, and a 6-membered heteroaromatic compound.

4. The process for the manufacture of a fluorinated compound according to claim 1, wherein the column reactor is a packed bed tower reactor which is packed with fillers resistant to elemental fluorine ($F_2$) and hydrogen fluoride (HF) and the packed bed tower reactor is a gas scrubber system which is packed with fillers resistant to elemental fluorine ($F_2$) and hydrogen fluoride (HF).

5. The process for the manufacture of a fluorinated compound according to claim 1, wherein the reaction is carried out with a counter-current flow of the circulating liquid medium of a) comprising the starting compound and of the fluorination gas of b) fed into the column reactor and which fluorination gas of b) comprises elemental fluorine ($F_2$).

6. The process for the manufacture of a fluorinated compound according to claim 4, wherein the fillers are Raschig fillers or metal fillers.

* * * * *